(12) United States Patent
McGowan et al.

(10) Patent No.: US 8,623,899 B2
(45) Date of Patent: *Jan. 7, 2014

(54) BIS-BENZIMIDAZOLE DERIVATIVES AS HEPATITIS C VIRUS INHIBITORS

(75) Inventors: David McGowan, Brussel (BE); Samuel Dominique Demin, Mechelen (BE); Stefaan Julien Last, Lint (BE); Koen Vandyck, Paal-Beringen (BE); Pierre Jean-Marie Bernard Raboisson, Rosieres (BE)

(73) Assignee: Janssen Research & Development Ireland, Little Island, Co Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/389,277

(22) PCT Filed: Aug. 6, 2010

(86) PCT No.: PCT/EP2010/061494
§ 371 (c)(1),
(2), (4) Date: Feb. 7, 2012

(87) PCT Pub. No.: WO2011/015658
PCT Pub. Date: Feb. 10, 2011

(65) Prior Publication Data
US 2012/0135953 A1   May 31, 2012

(30) Foreign Application Priority Data
Aug. 7, 2009  (EP) .................... 09167436

(51) Int. Cl.
*A61K 31/4184* (2006.01)
*C07D 403/10* (2006.01)
(52) U.S. Cl.
USPC ............... 514/394; 548/302.7; 548/305.4; 514/385
(58) Field of Classification Search
USPC .............. 548/301.7, 302.7, 304.4, 305.4; 514/385, 394
See application file for complete search history.

(56) References Cited

U.S. PATENT DOCUMENTS

| 8,088,368 | B2 * | 1/2012 | Guo et al. | 424/85.4 |
| 8,188,132 | B2 * | 5/2012 | Or et al. | 514/394 |
| 8,242,156 | B2 * | 8/2012 | Qiu et al. | 514/394 |
| 8,273,341 | B2 * | 9/2012 | Guo et al. | 424/85.4 |
| 8,314,135 | B2 * | 11/2012 | Qiu et al. | 514/394 |

FOREIGN PATENT DOCUMENTS

| WO | WO2006133326 A1 | 12/2006 |
| WO | WO2008021927 A2 | 2/2008 |
| WO | WO2008021928 A2 | 2/2008 |
| WO | WO2008048589 A2 | 4/2008 |
| WO | WO2008070447 A2 | 6/2008 |
| WO | WO2010017401 A1 | 2/2010 |
| WO | WO2010065681 A1 | 6/2010 |

OTHER PUBLICATIONS

Krieger, et al., Enhancement of Hepatitis C Virus RNA Replication by Cell Culture, Journal of Virology, May 1, 2001, 75-10, 4614-1624.
Lohmann, et al., Replication of Subgenomic Hepatitis C Virus RNAs in a Hepatoma Cell Line, Science, 1999, vol. 285, pp. 110-113.

* cited by examiner

*Primary Examiner* — Golam M M Shameem

(57) ABSTRACT

Inhibitors of HCV replication of formula I

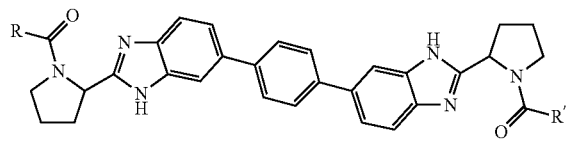

including stereochemically isomeric forms, and salts, hydrates, solvates thereof, wherein R and R' have the meaning as defined herein.
The present invention also relates to processes for preparing said compounds, pharmaceutical compositions containing them and their use, alone or in combination with other HCV inhibitors, in HCV therapy.

8 Claims, No Drawings

BIS-BENZIMIDAZOLE DERIVATIVES AS HEPATITIS C VIRUS INHIBITORS

This application is a national stage application of PCT/EP2010/061494, filed Aug. 6, 2010, which claims priority benefit of Application No. EP 09167436.6 filed Aug. 7, 2009. The complete disclosures of the aforementioned related patent applications are hereby incorporated herein by reference for all purposes.

TECHNICAL FIELD

This invention relates to bis-benzimidazole derivatives, which are inhibitors of the hepatitis C virus (HCV), their synthesis and their use, alone or in combination with other HCV inhibitors, in the treatment or prophylaxis of HCV.

BACKGROUND ART

HCV is a single stranded, positive-sense RNA virus belonging to the Flaviviridae family of viruses in the *hepacivirus* genus. The viral genome translates into a single open reading frame that encodes for multiple structural and non-structural proteins.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations.

There are six major HCV genotypes and more than 50 subtypes, which are differently distributed geographically. HCV genotype 1 is the predominant genotype in Europe and in the U.S. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in 40% of patients infected by genotype 1 HCV and about 80% of those infected by genotypes 2 and 3. Beside the limited efficacy on HCV genotype 1, this combination therapy has significant side effects including influenza-like symptoms, hematologic abnormalities, and neuropsychiatric symptoms. Hence there is a need for more effective, more convenient and better-tolerated treatments.

Experience with HIV drugs, in particular with HIV protease inhibitors, has taught that sub-optimal pharmacokinetics and complex dosing regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the pharmacokinetics and rate of drug metabolism necessary to allow such trough levels provides a stringent challenge to drug design.

The NS5A protein of HCV is located downstream of the NS4B protein and upstream of the NS5B protein. Upon post-translational cleavage by the viral serine protease NS3/4A, the NS5A matures into a zinc containing, three-domain phosphoprotein that either exists as a hypophosphorylated (56-kDa, p56) or hyperphosphorylated species (58-kDa, 58). NS5A of HCV is implicated in multiple aspects of the viral lifecycle including viral replication and infectious particle assembly as well as modulation of the environment of its host cell. Although no enzymatic function has been ascribed to the protein it is reported to interact with numerous viral and cellular factors.

A number of patents and patent applications disclose compounds with HCV inhibitory activity, in particular targeting NS5A. WO2006/133326 discloses stilbene derivatives while WO2008/021927 and WO2008/021928 disclose biphenyl derivatives having NS5A HCV inhibitory activity. WO2008/048589 discloses 4-(phenylethynyl)-1H-pyrazole derivatives and their antiviral use. WO2008/070447 discloses a broad range of HCV inhibiting compounds including a benzimidazole moiety. WO2010/017401 and WO2010/065681 both disclose bis-imidazole inhibitors of HCV NS5A.

There is a need for HCV inhibitors that may overcome the disadvantages of current HCV therapy such as side effects, limited efficacy, the emerging of resistance, and compliance failures, as well as improve the sustained viral load response.

The present invention concerns a group of HCV inhibiting bis-benzimidazole derivatives with useful properties regarding one or more of the following parameters: antiviral efficacy, favorable profile of resistance development, reduced or lack of toxicity and genotoxicity, favorable pharmacokinetics and pharmacodynamics, ease of formulation and administration, and limited or lack of drug-drug interactions with other drug substances, in particular other anti-HCV agents.

Compounds of the invention may also be attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

DESCRIPTION OF THE INVENTION

In one aspect, the present invention provides compounds which can be represented by the formula I:

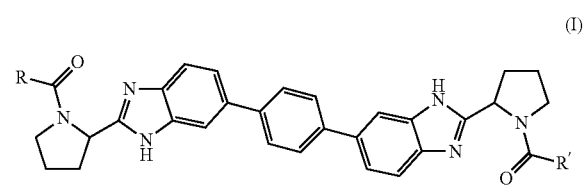

including any possible stereoisomers thereof, wherein:
R and R' are independently selected from —CR$_1$R$_2$R$_3$, aryl optionally substituted with 1 or 2 substituents selected from halo and methyl, and heteroC$_{4-7}$cycloalkyl, wherein R$_1$ is selected from C$_{1-4}$alkyl optionally substituted with methoxy, hydroxyl or dimethylamino; C$_{3-6}$cycloalkyl; tetrahydropyranyl; phenyl optionally substituted with 1, 2 or 3 substituents independently selected from halo, $C_{1-4}$alkoxy, trifluoromethoxy or 2 substituents on adjacent ring atoms form a 1,3-dioxolane group; benzyl optionally substituted with halo or methoxy; heteroaryl; and heteroarylmethyl;

$R_2$ is selected from hydrogen, hydroxyl, amino, mono- and di-$C_{1-4}$alkylamino, ($C_{3-6}$cycloalkyl)($C_{1-4}$alkyl)amino, $C_{1-4}$alkylcarbonylamino, phenylamino, $C_{1-4}$alkyloxycarbonylamino, ($C_{1-4}$alkyloxycarbonyl)($C_{1-4}$alkyl)amino, $C_{1-4}$alkylaminocarbonylamino, tetrahydro-2-oxo-1(2H)-pyrimidinyl, pyrrolidin-1-yl, piperidin-1-yl, 3,3-difluoropiperidin-1-yl, morpholin-1-yl, 7-azabicyclo[2.2.1]hept-7-yl, and imidazol-1-yl; and $R_3$ is hydrogen or $C_{1-4}$alkyl, or $CR_2R_3$ together forms carbonyl; or $CR_1R_3$ forms a cyclopropyl group;

and the pharmaceutically acceptable salts and the solvates thereof.

In a further aspect, the invention concerns the use of compounds of formula I, or subgroups thereof, as specified herein, for inhibiting HCV. Alternatively, there is provided the use of said compounds for the manufacture of a medicament for inhibiting HCV.

Embodiments of the present invention concern compounds of formula (I), or any subgroup thereof as defined herein, wherein one or more of the definitions for R, R', $R_1$, $R_2$ and $R_3$ as specified herein, apply.

Subgroups of compounds of formula I are those compounds of formula I, or subgroups of compounds of formula I, as defined herein, wherein R and R' are independently —$CR_1R_2R_3$ or aryl wherein aryl is 5-membered heteroaryl; in particular, wherein R and R' are independently —$CR_1R_2R_3$; more in particular, wherein R and R' are —$CR_1R_2R_3$ and are the same.

Subgroups of compounds of formula I are those compounds of formula I, or subgroups of compounds of formula I, as defined herein, wherein $R_2$ is hydroxyl, amino, mono- or di-$C_{1-4}$alkylamino, $C_{1-4}$alkylcarbonylamino, $C_{1-4}$alkyloxycarbonylamino; in particular, $R_2$ is $C_{1-4}$alkylcarbonylamino or $C_{1-4}$alkyloxycarbonylamino.

Subgroups of compounds of formula I are those compounds of formula I, or subgroups of compounds of formula I, as defined herein, wherein $R_1$ is selected from $C_{1-4}$alkyl; phenyl optionally substituted with 1 or 2 substituents independently selected from halo, methyl, methoxy or 2 substituents on adjacent ring atoms form a 1,3-dioxolane group; and heteroaryl. In particular, $R_1$ is selected from branched $C_{3-4}$alkyl; phenyl optionally substituted with 1 substituent selected from halo and methyl; and heteroaryl. More in particular, $R_1$ is selected from branched $C_{3-4}$alkyl; phenyl optionally substituted with 1 substituent selected from halo.

In a first embodiment,

R and R' are independently selected from —$CR_1R_2R_3$, aryl optionally substituted with 1 or 2 substituents selected from halo and methyl, and hetero$C_{4-7}$cycloalkyl, wherein $R_1$ is selected from $C_{1-4}$alkyl optionally substituted with methoxy or dimethyl-amino; phenyl optionally substituted with 1, 2 or 3 substituents independently selected from halo, $C_{1-4}$alkoxy, trifluoromethoxy or 2 substituents on adjacent ring atoms form a 1,3-dioxolane group; benzyl optionally substituted with halo or methoxy; heteroaryl; and heteroarylmethyl;

$R_2$ is selected from hydrogen, hydroxyl, amino, mono- and di-$C_{1-4}$alkylamino, $C_{1-4}$alkylcarbonylamino, $C_{1-4}$alkyloxycarbonylamino, $C_{1-4}$alkylaminocarbonyl-amino, piperidin-1-yl and imidazol-1-yl; and $R_3$ is hydrogen, or $R_1$ and $R_3$ together form an oxo or a cyclopropyl group; or a pharmaceutically acceptable salt and/or solvate thereof.

In a second embodiment, R and R' are independently selected from —$CR_1R_2R_3$, aryl optionally substituted with 1 or 2 substituents selected from halo and methyl, and hetero$C_{4-7}$cycloalkyl, wherein $R_1$ is selected from $C_{1-4}$alkyl optionally substituted with methoxy, hydroxyl or dimethylamino; $C_{3-6}$cycloalkyl; phenyl optionally substituted with 1, 2 or 3 substituents independently selected from halo, $C_{1-4}$alkoxy, trifluoromethoxy or 2 substituents on adjacent ring atoms form a 1,3-dioxolane group; benzyl optionally substituted with halo or methoxy; heteroaryl; and heteroarylmethyl;

$R_2$ is selected from hydrogen, hydroxyl, amino, mono- and di-$C_{1-4}$alkylamino, ($C_{3-6}$cycloalkyl)($C_{1-4}$alkyl)amino, $C_{1-4}$alkylcarbonylamino, phenylamino, $C_{1-4}$alkyloxycarbonylamino, ($C_{1-4}$alkyloxycarbonyl)($C_{1-4}$alkyl)amino, $C_{1-4}$alkylaminocarbonylamino, tetrahydro-2-oxo-1(2H)-pyrimidinyl, pyrrolidin-1-yl, piperidin-1-yl, 3,3-difluoropiperidin-1-yl, morpholin-1-yl, 7-azabicyclo[2.2.1]hept-7-yl, and imidazol-1-yl; and $R_3$ is hydrogen or $C_{1-4}$alkyl, or $CR_2R_3$ together forms carbonyl; or $CR_1R_3$ forms a cyclopropyl group;

and the pharmaceutically acceptable salts and the solvates thereof;

provided that (a) when R and R' are identical and represent —$CR_1R_2R_3$ wherein (a-1) $R_2$ is $C_{1-4}$alkyloxycarbonylamino and $R_3$ is hydrogen, then $R_1$ is other than unsubstituted $C_{1-4}$alkyl, or ethyl substituted with hydroxyl or methoxy; or wherein (a-2) $R_2$ is methyloxycarbonylamino and $R_3$ is hydrogen, then $R_1$ is other than unsubstituted phenyl; and (b) when R and R' are different and each independently represent —$CR_1R_2R_3$, wherein $R_1$ is phenyl or 2-propyl, $R_2$ is dimethylamine and $R_3$ is hydrogen in one —$CR_1R_2R_3$ group, then the other —$CR_1R_2R_3$ group cannot take the meaning of $R_1$ being 2-propyl and $R_2$ being methyloxycarbonylamino and $R_3$ being hydrogen.

In a third embodiment, R and R' are independently selected from —$CR_1R_2R_3$, wherein $R_1$ is selected from phenyl optionally substituted with 1, 2 or 3 substituents independently selected from halo, $C_{1-4}$alkoxy, trifluoromethoxy or 2 substituents on adjacent ring atoms form a 1,3-dioxolane group;

$R_2$ is selected from hydroxyl, mono- or di-$C_{2-4}$alkylamino, ($C_{3-6}$cycloalkyl)($C_{1-4}$alkyl)-amino, $C_{1-4}$alkylcarbonylamino, ($C_{1-4}$alkyloxycarbonyl)($C_{1-4}$alkyl)amino, $C_{1-4}$alkyl-aminocarbonylamino, tetrahydro-2-oxo-1(2H)-pyrimidinyl, pyrrolidin-1-yl, piperidin-1-yl, 3,3-difluoropiperidin-1-yl, morpholin-1-yl, 7-azabicyclo[2.2.1]hept-7-yl, and imidazol-1-yl; and $R_3$ is hydrogen or $C_{1-4}$alkyl, or $CR_2R_3$ together forms carbonyl; or $CR_1R_3$ forms a cyclopropyl group;

and the pharmaceutically acceptable salts and the solvates thereof;

In a fourth embodiment, $R^1$ is selected from heteroaryl; and heteroarylmethyl; $R_2$ is selected from hydrogen, mono- or di-$C_{1-4}$alkylamino, ($C_{3-6}$cycloalkyl)($C_{1-4}$alkyl)-amino, $C_{1-4}$alkylcarbonylamino, $C_{1-4}$alkyloxycarbonylamino, ($C_{1-4}$alkyloxycarbonyl) ($C_{1-4}$alkyl)amino, $C_{1-4}$alkylaminocarbonylamino, tetrahydro-2-oxo-1(2H)-pyrimidinyl, pyrrolidin-1-yl, piperidin-1-yl, 3,3-difluoropiperidin-1-yl, morpholin-1-yl, 7-azabicyclo[2.2.1]hept-7-yl, and imidazol-1-yl; and $R_3$ is hydrogen;

and the pharmaceutically acceptable salts and the solvates thereof.

In a fifth embodiment,
$R_1$ is $C_{1-4}$alkyl;
$R_2$ is selected from $C_{1-4}$alkylaminocarbonylamino, or tetrahydro-2-oxo-1(2H)-pyrimidinyl; and
$R_3$ is hydrogen or $C_{1-4}$alkyl;
and the pharmaceutically acceptable salts and the solvates thereof.

In a sixth embodiment
$R_1$ is $C_{3-6}$cycloalkyl;
$R_2$ is hydrogen
and $R_3$ is hydrogen;
and the pharmaceutically acceptable salts and the solvates thereof.

In a further aspect, the invention provides a compound of formula I or a pharmaceutically acceptable salt, hydrate, or solvate thereof, for use in the treatment or prophylaxis (or the manufacture of a medicament for the treatment or prophylaxis) of HCV infection. Representative HCV genotypes in the context of treatment or prophylaxis in accordance with the invention include but are not limited to genotype 1b (prevalent in Europe) and 1a (prevalent in North America). The invention also provides a method for the treatment or prophylaxis of HCV infection, in particular of the genotype 1a or 1b, comprising administering to a subject in need thereof, a therapeutically effective amount of a compound as defined hereinbefore.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms or stereoisomers of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereoisomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography or supercritical fluid chromatography.

The compounds of formula have several centers of chirality. Of interest are the stereogenic centers of the pyrrolidine ring at the 2-carbon atom. The configuration at this position may be that corresponding to L-proline, i.e.

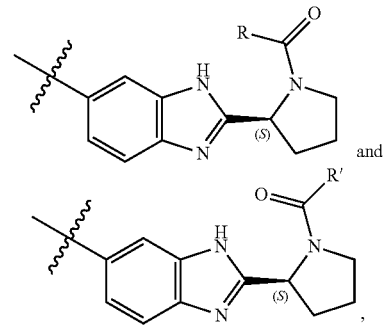

and or that corresponding to D-proline, i.e.

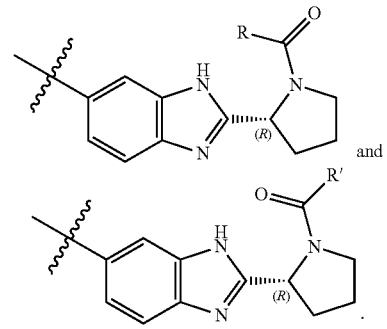

and

Of particular interest are compounds of formula I or subgroups thereof as defined herein, that are according to formula Ia.

Ia

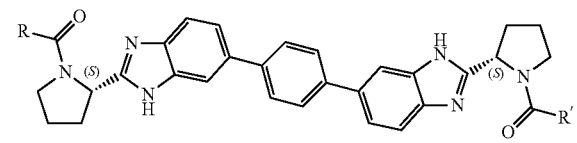

Also of interest is the configuration of the group —$CR_1R_2R_3$: when $R_1$ is selected from $C_{1-4}$alkyl optionally substituted with methoxy, hydroxyl or dimethylamino; $C_{3-6}$cycloalkyl; and tetrahydropyranyl, then the S-configuration is preferred; when $R_1$ is selected from phenyl optionally substituted with 1, 2 or 3 substituents independently selected from halo, $C_{1-4}$alkoxy, trifluoromethoxy or 2 substituents on adjacent ring atoms form a 1,3-dioxolane group; and heteroaryl; then the R-configuration is preferred.

The pharmaceutically acceptable addition salts comprise the therapeutically active non-toxic acid and base addition salt forms of the compounds of formula (I) or subgroups thereof. Of interest are the free, i.e. non-salt forms of the compounds of formula I, or of any subgroup of compounds of formula I specified herein.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their base addition salts, in particular metal or amine addition salt forms, by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvates that the compounds of formula I as well as the salts thereof, are able to form. Such solvates are for example hydrates, alcoholates, e.g. ethanolates, propanolates, and the like.

Some of the compounds of formula I may also exist in tautomeric forms. For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

As used herein, "$C_{1-4}$alkyl" as a group or part of a group defines saturated straight or branched chain hydrocarbon groups having from 1 to 4 carbon atoms such as for example methyl, ethyl, 1-propyl, 2-propyl, 1-butyl, 2-butyl, 2-methyl-1-propyl, 2-methyl-2-propyl. For the purpose of the present invention, of interest amongst $C_{1-4}$alkyl is $C_{3-4}$alkyl, i.e. straight or branched chain hydrocarbon groups having 3 or 4 carbon atoms such as 1-propyl, 2-propyl, 1-butyl, 2-butyl, 2-methyl-1-propyl, 2-methyl-2-propyl. Of particular interest may be branched $C_{3-4}$alkyl such as 2-propyl, 2-butyl, 2-methyl-1-propyl, 2-methyl-2-propyl.

The term "$C_{3-6}$cycloalkyl" as a group or part thereof, defines saturated cyclic hydrocarbon groups having from 3 to 6 carbon atoms that together form a cyclic structure. Examples of $C_{3-6}$cycloalkyl include cyclopropyl, cyclobutyl, cyclopentyl and cyclohexyl.

"$C_{1-4}$alkoxy" as a group or part of a group means a group of formula —O—$C_{1-4}$alkyl wherein $C_{1-4}$alkyl is as defined above. Examples of $C_{1-4}$alkoxy are methoxy, ethoxy, n-propoxy, isopropoxy.

The term "halo" is generic to fluoro, chloro, bromo and iodo.

As used herein, the term "(=O)" or "oxo" forms a carbonyl moiety when attached to a carbon atom. It should be noted that an atom can only be substituted with an oxo group when the valency of that atom so permits.

As used herein for the purpose of defining "aryl" as a group or part thereof means an aromatic ring structure optionally comprising one or two heteroatoms selected from N, O and S, in particular from N and O. Said aromatic ring structure may have 5 or 6 ring atoms.

As used herein, the prefix "hetero-" in the definition of a group means that the group comprises at least 1 heteroatom selected from N, O and S, in particular N and O. For example, the term "heteroaryl" means an aromatic ring structure as defined for the term "aryl", comprising at least 1 heteroatom selected from N, O and S, in particular from N and O, for example furanyl, oxazolyl, pyridinyl. Alternatively, the term "hetero$C_{4-7}$cycloalkyl" means saturated cyclic hydrocarbon groups comprising at least 1 heteroatom selected from N, O and S, in particular from N and O, for example tetrahydrofuranyl, tetrahydropyranyl, piperidinyl.

Where the position of a group on a molecular moiety is not specified (for example a substituent on phenyl) or is represented by a floating bond, such group may be positioned on any atom of such a moiety, as long as the resulting structure is chemically stable. When any variable is present more than once in the molecule, each definition is independent.

Whenever used herein, the term "compounds of formula I", or "the present compounds" or similar terms, it is meant to include the compounds of formula I, including the possible stereoisomeric forms, and the pharmaceutically acceptable salts and solvates thereof.

General Synthetic Methods

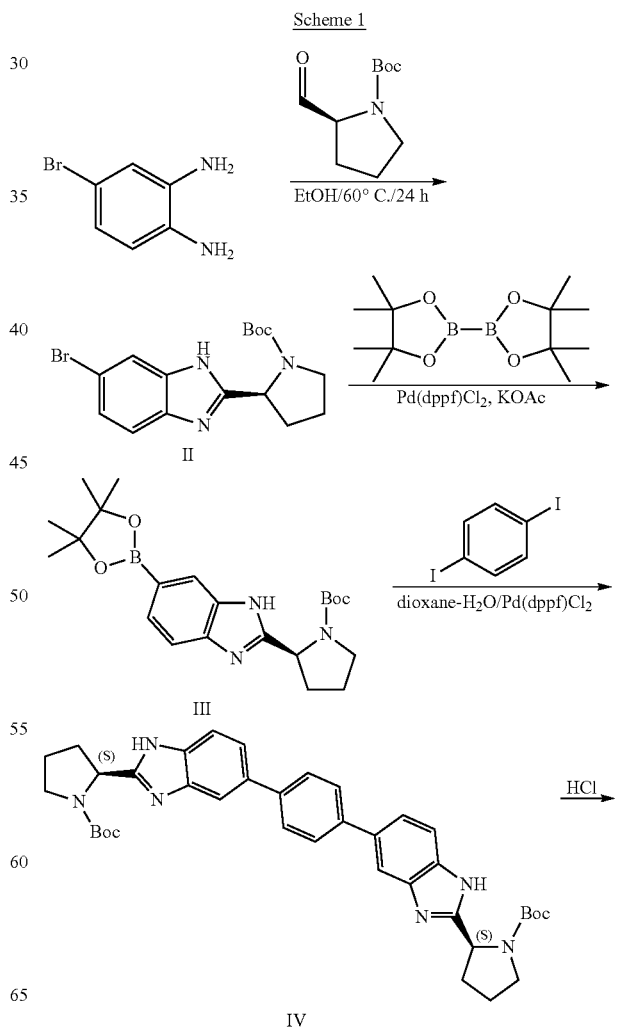

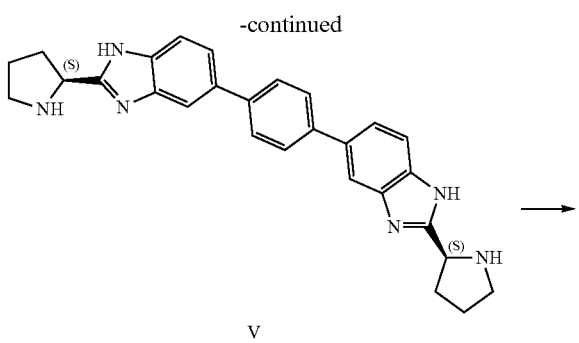

V

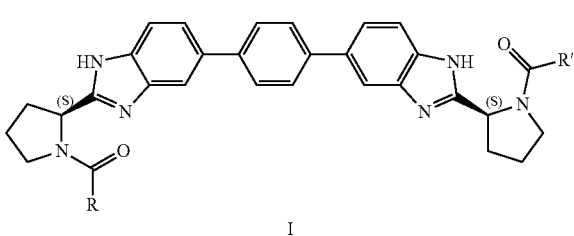

I

Compounds of formula I wherein R and R' are the same, can be obtained using the synthetic pathway illustrated in the scheme 1 above. Oxidative cyclisation of N-(tert-Butoxycarbonyl)-L-prolinal with 4-bromobenzene-1,2-diamine, results in benzimidazole derivative II, which is converted to boronic ester III under Pd catalyzed conditions in the presence of bis(pinacolato)diboron. Subsequently, boronic ester III is converted to compound IV, by coupling with 1,4-diiodobenzene, using Suzuki-Miyaura conditions. Alternatively, 1,4-dibromobenzene may used instead of 1,4-diiodobenzene. A suitable Pd catalyst is dichloro-((bis-diphenylphosphino)ferrocenyl)palladium(II) (Pd(dppf)Cl$_2$). Compound V is obtained after removal of the tert-butoxycarbonyl (Boc) protecting group of the pyrrolidine nitrogen under acidic conditions, for example using HCl in isopropanol. The resulting compound V may then be converted to a compound of formula I by acylation with the appropriate acid of formula R—C(=O)—OH wherein R has the meanings of R and R' as defined for the compounds of formula I or any subgroup thereof.

Said acylation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions for amino-group acylation or amide bond formation include the azide method, mixed carbonic-carboxylic acid anhydride (isobutyl chloroformate) method, the carbodiimide (dicyclohexylcarbodiimide, diisopropyl-carbodiimide, or water-soluble carbodiimide such as N-ethyl-N'-[3-(dimethylamino)-propyl]carbodiimide) method, the active ester method (e.g. p-nitrophenyl, p-chlorophenyl, trichlorophenyl, pentachloro-phenyl, pentafluorophenyl, N-hydroxysuccinic imido and the like esters), the Woodward reagent K-method, the 1,1-carbonyldiimidazole (CDI or N,N'-carbonyl-diimidazole) method, the phosphorus reagents or oxidation-reduction methods. Some of these methods can be enhanced by adding suitable catalysts, e.g. in the carbodiimide method by adding 1-hydroxybenzotriazole, or 4-DMAP. Further coupling agents are (benzotriazol-1-yloxy)-tris-(dimethylamino) phosphonium hexafluorophosphate, either by itself or in the presence of 1-hydroxy-benzotriazole or 4-DMAP; or 2-(1H-benzotriazol-1-yl)-N,N,N',N'-tetramethyluronium tetrafluoroborate (TBTU), or O-(7-azabenzotriazol-1-yl)-N,N,N'N'-tetramethyluronium hexafluorophosphate (HATU). These coupling reactions can be performed in either solution (liquid phase) or solid phase. For the purpose of the present invention, a preferred method for acylation is performed employing HATU.

The coupling reactions preferably are conducted in inert solvents, such as halogenated hydrocarbons, e.g. dichloromethane, chloroform, dipolar aprotic solvents such as acetonitrile, dimethylformamide, dimethylacetamide, DMSO, HMPT, or ethers such as tetrahydrofuran (THF).

In many instances the coupling reactions are conducted in the presence of a suitable base such as a tertiary amine, e.g. triethylamine, diisopropylethylamine (DIPEA), N-methylmorpholine, N-methylpyrrolidine, 4-DMAP or 1,8-diazabicyclo[5.4.0]undec-7-ene (DBU). The reaction temperature may range between 0° C. and 50° C. and the reaction time may range between 15 min and 24 h.

Scheme 2

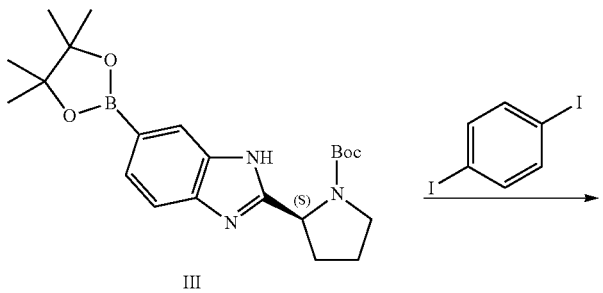

III

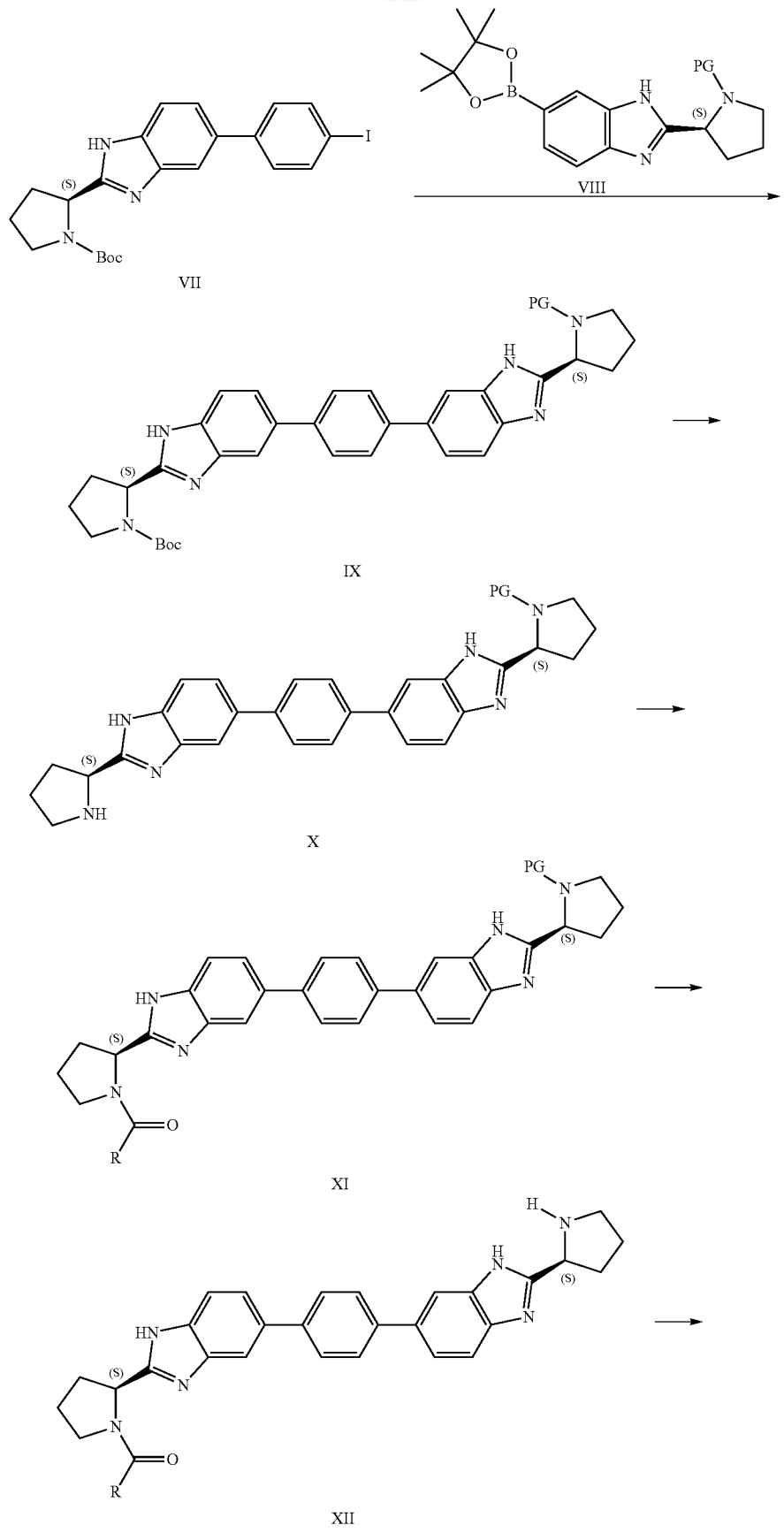

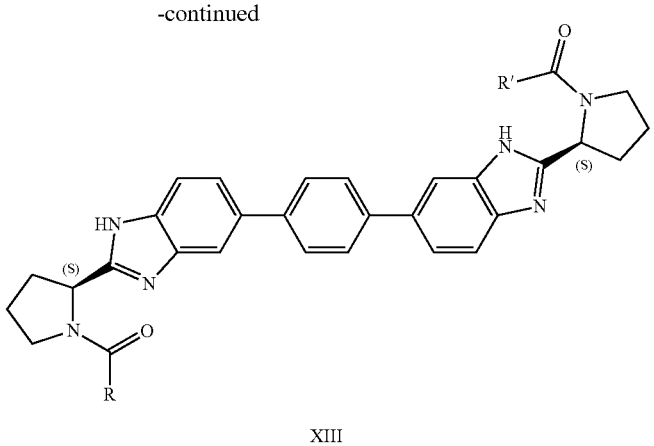

XIII

Alternatively, compounds of formula I wherein R and R' are not the same, i.e. compounds of formula XIII, may be obtained using the synthetic pathway illustrated in scheme 2. Using standard Suzuki-Miyaura conditions, boronic ester III and 1,4-diiodobenzene can be coupled, under conditions comparable to those used in the conversion of III to IV (scheme 1), except that the ratio of 1,4-diiodobenzene to boronic ester III is around 1 to 1, possibly higher, to obtain mono iodide VII. Alternatively, 1,4-dibromobenzene may be used instead of 1,4-diiodobenzene. VII can then be coupled with boronic ester VIII. It should be understood that the amino protecting group PG on the pyrrolidine nitrogen in boronic ester VIII should be selected so that it can be removed under conditions that do not affect a Boc-group or an R—C(=O)— group on another nitrogen in the molecule. It should also be understood that PG may as well be the R'—C(=O)— group of the final compound of formula I being synthesized. Coupling VII and VIII may again be performed by using standard Suzuki-Miyaura conditions, and results in compound IX. Compound IX can then selectively be deprotected to compound X by using conditions appropriate to remove the Boc protecting group. For example, in case PG is benzyloxycarbonyl or benzyl, the Boc protecting group may by selectively removed under standard Boc-deprotection conditions, i.e. acid treatment.

Furthermore, in case PG is benzyloxycarbonyl or benzyl, PG may be selectively removed under reductive treatment leaving the R—C(=O)— group in compound XI intact. Other suitable protection groups PG and concomittant selective deprotection conditions can be sourced from Greene's "Protective groups in organic synthesis" by Peter G. M. Wuts, Fourth Edition, Chapter 7: 'Protection for the Amino group'.

Compound X can subsequently be acylated with the appropriate acid of formula R—C(=O)—OH wherein R has the meanings of R as defined for the compounds of formula I or any subgroup thereof. Compound XI is obtained.

For compound XI, in case PG represents —(C=O)—R', compound XI equals compound XIII. In case PG represents an amino protecting group, PG can be removed under conditions compatible with —(C=O)—R, for example hydrogenation when PG is benzyl or benzyloxycarbonyl or basic conditions like diethylamine in case PG is fluorenylmethyloxycarbonyl, resulting in compound XII. Other selective deprotections can be sourced from Greene's reference book.

In case —(C=O)—R is not compatible with the PG deprotection conditions, the route depicted in scheme 5 could be used, where the protecting group PG is chosen to be compatible with the Boc group.

Compounds XII can be transformed in compound XIII, by acylation similar to the conversion of XIV to XV, V to I and X to XI, and as described in detail for the conversion of V to I under scheme 1.

Scheme 3

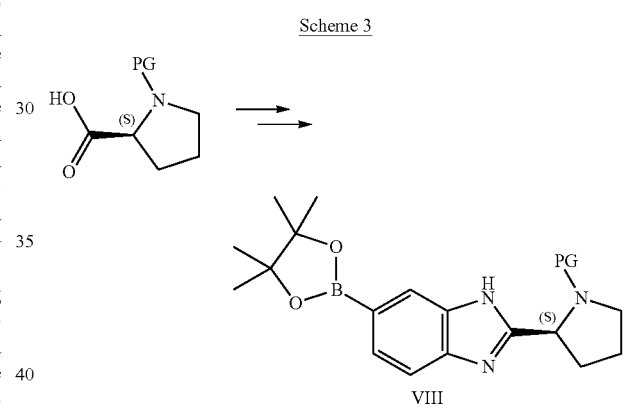

Scheme 4

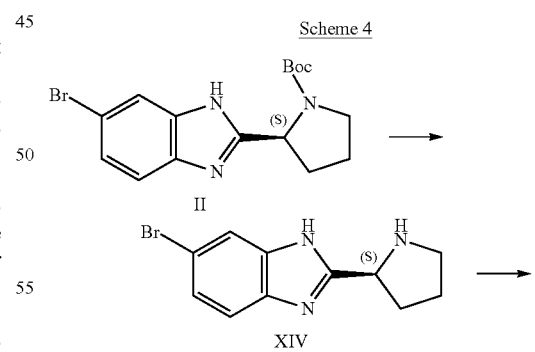

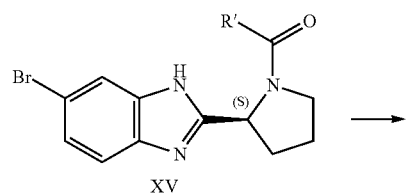

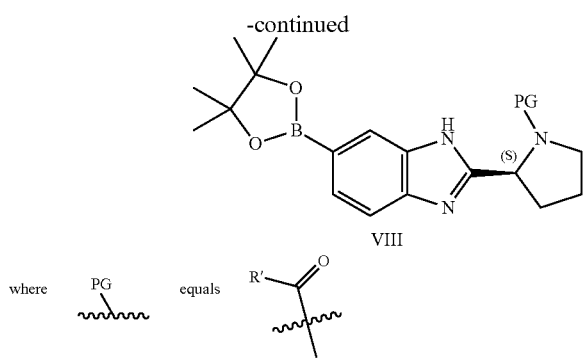

where PG equals

The boronic ester VIII can be obtained by at least two different routes as illustrated in schemes 3 and 4. In case PG represents a protecting group like for example benzyloxycarbonyl, fluorenylmethyloxycarbonyl, benzyl, or another suitable protection group PG as described in Greene's reference book, the compound can be synthesized by methods used for the synthesis of intermediate compounds II and IIa (see example 2), and boronic ester III, starting from the correspondingly protected pyrrolidine derivative. In case PG represents —(C=O)—R', the compound can be made from intermediate II, as shown in scheme 4, by deprotection of the proline nitrogen under acidic conditions, such as treatment with HCl in for example iPrOH or trifluoroacetic acid resulting in compound XIV, followed by coupling under standard acylation conditions, like the use of HATU in presence of a base like DIPEA. Next, the obtained bromide XV can be transformed in boronic acid VIII (where PG represents —(C=O)—R'), like for example the transformation of II to III.

tective group, for example hydrogenation when PG is benzyl or benzyloxycarbonyl or basic conditions like diethylamine in case PG is fluorenylmethyloxycarbonyl, resulting in compound XVI. Other selective deprotections can be sourced from Green's reference book. In this case, compound XVI equals compound X, with PG being Boc. In this case, deprotection from XI to XII can be achieved under conditions similar like in the conversion of II to XIV and IV to V.

The synthesis procedures as depicted above in schemes 1 to 5 may also be performed using racemic proline derivatives or D-proline derivatives instead of L-proline. Thereby, compounds of formula I with alternative stereochemistry may be obtained.

In a further aspect, the present invention concerns a pharmaceutical composition comprising a therapeutically effective amount of a compound of formula I as specified herein, and a pharmaceutically acceptable carrier. A therapeutically effective amount in this context is an amount sufficient to stabilize or to reduce HCV infection in infected subjects, or an amount sufficient to prevent HCV infection in subjects at risk of being infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addi- Scheme 5

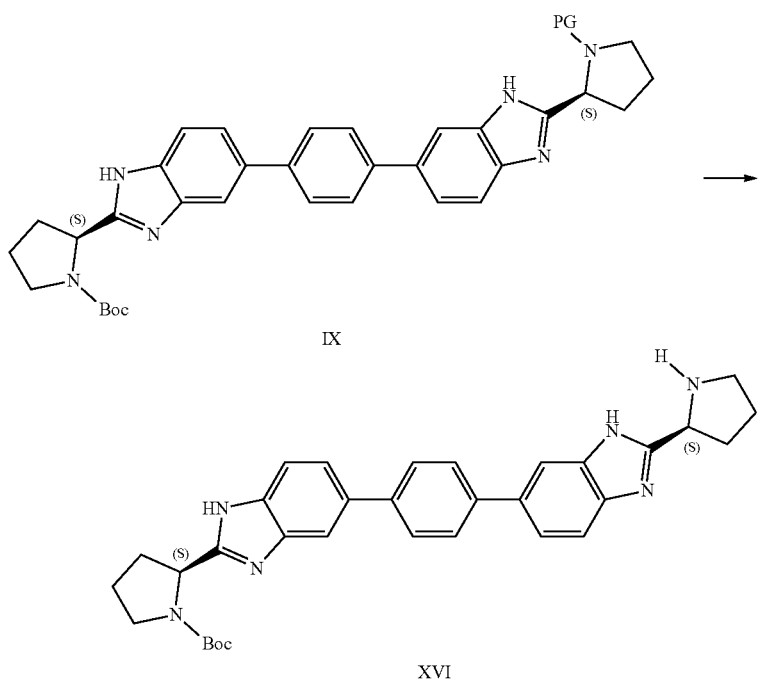

Alternatively, as shown in scheme 5, compound IX can be deprotected under conditions compatible with the Boc protion salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I show activity against HCV and can be used in the treatment and prophylaxis of HCV infection or diseases associated with HCV. The latter include progressive liver fibrosis, inflammation and necrosis leading to cirrhosis, end-stage liver disease, and hepatocellular carcinoma. A number of the compounds of this invention moreover are known to be active against mutated strains of HCV. Additionally, compounds of this invention may have attractive properties in terms of bioavailability, show a favorable pharmacokinetic profile, including an acceptable half-life, AUC (area under the curve), peak and trough values, and lack unfavorable phenomena such as insufficiently rapid onset or tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration.

Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their anti-HCV properties, the compounds of formula I or subgroups thereof, as specified herein, are useful in the inhibition of HCV replication, in particular in the treatment of warm-blooded animals, in particular humans, infected with HCV, and for the prophylaxis of HCV infections in warm-blooded animals, in particular humans. The present invention furthermore relates to a method of treating a warm-blooded animal, in particular a human, infected by HCV, or being at risk of infection by HCV, said method comprising the administration of a therapeutically or prophylactively effective amount of a compound of formula I, as defined hereinbefore.

The compounds of formula I as specified herein may therefore be used as a medicine, in particular as an anti-HCV medicine. Said use as a medicine or method of treatment comprises the systemic administration to HCV infected subjects or to subjects susceptible to HCV infection of an amount effective to relieve or prevent the symptoms and conditions associated with HCV infection.

The present invention also relates to the use of the present compounds in the manufacture of a medicament for the treatment or the prevention of HCV infection.

In general it is contemplated that an effective antiviral daily amount would be from about 0.01 to about 50 mg/kg, or about 0.02 to about 30 mg/kg body weight. It may be appropriate to administer the required dose as two, three, four or more sub-doses at appropriate intervals throughout the day. Said sub-doses may be formulated as unit dosage forms, for example, containing about 1 to about 1000 mg, or about 1 to about 500 mg, or about 1 to about 100 mg, or about 2 to about 50 mg of active ingredient per unit dosage form.

Combination Therapy

The invention also relates to a combination of a compound of formula I, a pharmaceutically acceptable salt or solvate thereof, and another antiviral compound, in particular another anti-HCV compound. The term "combination" relates to a product containing (a) a compound of formula I, as defined hereinbefore, and (b) another anti-HCV inhibitor, as a combined preparation for simultaneous, separate or sequential use in the treatment of HCV infections.

The combinations of the present invention may be used as medicaments. Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy in particular comprising a compound of formula (I) and at least one other anti-HCV agent, e.g. IFN-α, pegylated IFN-α, ribavirin, albuferon, taribavirin, nitazoxanide Debio025 or a combination thereof.

Other agents that may be combined with the compounds of the present invention include, for example, nucleoside and non-nucleoside inhibitors of the HCV polymerase, protease inhibitors, helicase inhibitors, NS4B inhibitors and agents that functionally inhibit the internal ribosomal entry site (IRES) and other agents that inhibit HCV cell attachment or virus entry, HCV RNA translation, HCV RNA transcription, replication or HCV maturation, assembly or virus release. Specific compounds in these classes include HCV protease inhibitors such as telaprevir (VX-950), boceprevir (SCH-503034), narlaprevir (SCH-900518), ITMN-191 (R-7227), TMC435350 (TMC435), MK-7009, BI-201335, BI-2061 (ciluprevir), BMS-650032, ACH-1625, ACH-1095, GS 9256, VX-985, IDX-375 (HCV NS4A protease co-factor inhibitor), VX-500, VX-813, PHX-1766, PHX2054, IDX-136, IDX-316, ABT-450, EP-013420 (and congeners) and VBY-376; the nucleoside HCV polymerase inhibitors useful in the invention include R7128, PSI-7851, PSI 7977, IDX-189, IDX-184, IDX-102, R1479, UNX-08189, PSI-6130, PSI-938 and PSI-879 and various other nucleoside and nucleotide analogs and HCV inhibitors including those derived as 2'-C-methyl modified nucleosides, 4'-aza modified nucleosides, and 7'-deaza modified nucleosides, e.g. 4-amino-1-[5-azido-4-hydroxy-5-hydroxymethyl-3-methyltetrahydrofuran-2-yl]-pyrimidin-2(1H)-one (Ref 1) and the bis-2-methylpropanoate ester thereof (Ref 2). Non-nucleoside HCV polymerase inhibitors useful in the invention include HCV-796, HCV-371, VCH-759, VCH-916, VCH-222, ANA-598, MK-3281, ABT-333, ABT-072, PF-00868554, BI-207127, GS-9190, A-837093, JKT-109, GL-59728, GL-60667, ABT-072, AZD-2795 and 13-cyclohexyl-3-methoxy-17,23-dimethyl-7H-10,6-(methanoiminothioiminoethanooxyethanoiminomethano)indolo[2,1-a][2]benzazepine-14,24-dione 16,16-dioxide (Ref 3).

The following examples are meant to illustrate the invention and should not be construed as a limitation of its scope.

EXAMPLES

Example 1

Synthesis of the Compound V 1.1 Preparation of Intermediate II

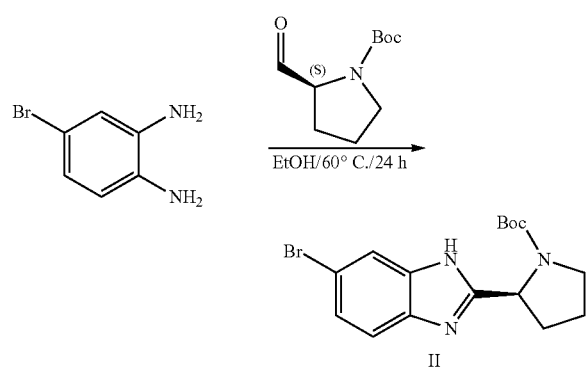

To a solution of 4-bromobenzene-1,2-diamine (170 g, 0.91 mol) in ethanol (2 L) was added (S)-tert-butyl 2-formylpyrrolidine-1-carboxylate (258 g, 1.3 mol) at 25° C., the mixture was heated to 60° C. for 24 hours, TLC shows reaction was complete. The solution was concentrated and the crude product was purified by column chromatography (petroleum ether: ethyl acetate 10:1 to 2:1) to afford 215 g of II as a yellow solid.

$^1$H NMR: CDCl$_3$ 400 MHz
δ7.95-7.4 (m, 3H), 5.35-5.25 (m, 1H), 3.85-3.70 (m, 1H), 3.6-3.45 (m, 1H), 2.6-2.45 (m, 1H), 2.20-1.95 (m, 3H), 1.48-1.38 (m, 5H), 1.2-1.1 (m, 4H)

1.2 Preparation of Intermediate III

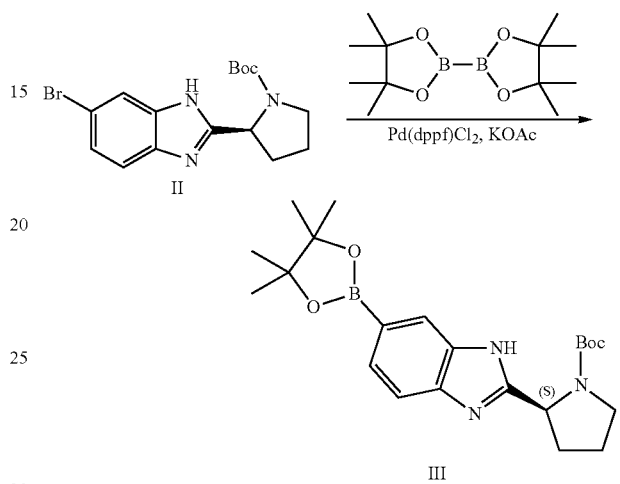

To a mixture of II (200 g, 546 mmol), potassium acetate (160.8 g, 1.64 mol) and 4,4,4',4',5,5,5',5'-octamethyl-2,2'-bi(1,3,2-dioxaborolane) (416 g, 1.64 mol) in DMF (3 L) was added Pd(dppf)Cl$_2$ (20 g) under nitrogen gas. The reaction mixture was stirred at 85° C. for 15 hours. The mixture was diluted with ethyl acetate, washed with water and brine, dried over magnesium sulfate, the solids removed by filtration, and the solvents of the filtrate were removed under reduced pressure. The residue was purified by silica column chromatography (petroleum ether: ethyl acetate 10:1 to 2:1) to afford 125 g of III as a white solid (contains 15% of boronic acid).

1.3 Preparation of Intermediate IV

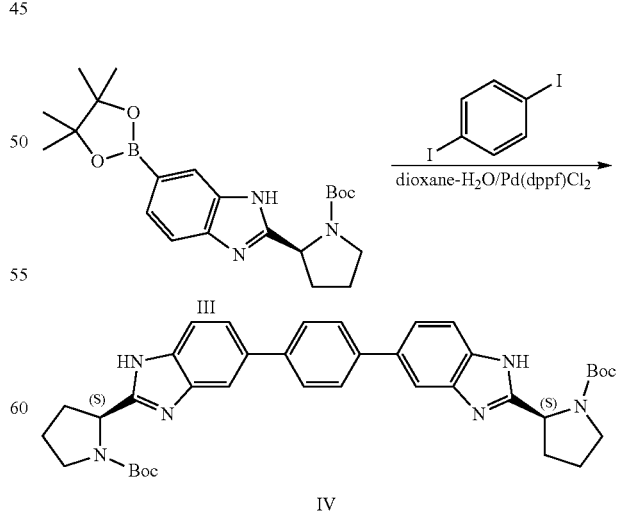

To the solution of 1,4-diiodobenzene (1.7 g, 5.15 mmol), III (6 g, 14.4 mmol) and K$_2$CO$_3$ (2.14 g, 15.5 mmol) in dioxane-H$_2$O (50 mL, 5:1) was added Pd(dppf)Cl$_2$ (300 mg) under nitrogen. The mixture was heated to 85° C. for 15 hours. The mixture was cooled to room temperature, concentrated, water was added and the mixture was extracted with ethyl acetate, dried over magnesium sulfate, the solids were removed via filtration, and the solvents of the filtrate were removed under reduced pressure. The crude product was purified by reverse phase HPLC to give 2 g, 96% of (IV).

$^1$H NMR: d-methanol 400 MHz
δ7.84-7.70 (m, 6H), 7.67-7.52 (m, 4H), 5.15-4.99 (m, 2H), 3.70-3.83 (m, 2H), 3.62-3.52 (m, 2H), 2.54-2.35 (m, 2H), 2.19-1.93 (m, 6H), 1.44-1.54 (m, 6H), 1.12-1.25 (m, 12H)

1.4 Preparation of Intermediate V

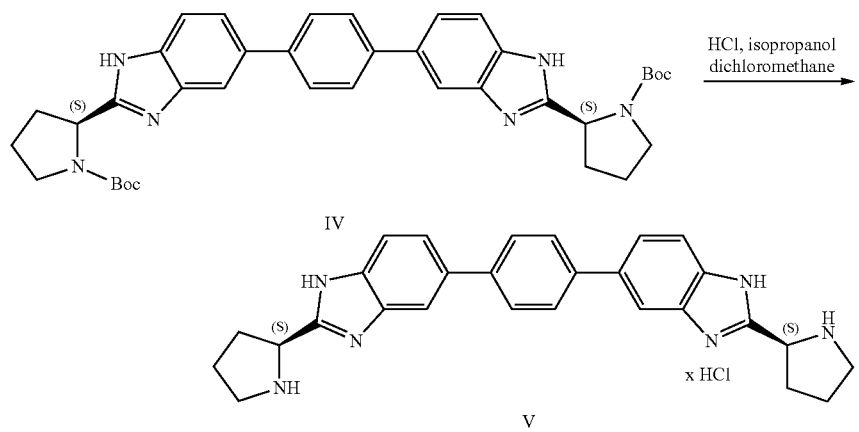

Into a 20 mL vial was placed IV (500 mg), dichloromethane (3 mL), and HCl in isopropanol (3 mL of 5 to 6M solution, Acros). This mixture is allowed to stir 4 hours at room temperature, LCMS confirmed complete conversion to V. The solvent was removed azeotropically under reduced pressure with toluene and methanol to afford a tan solid, which was used as such in the next step.

Example 2

Preparation of IIA, a Benzyl Protected Intermediate

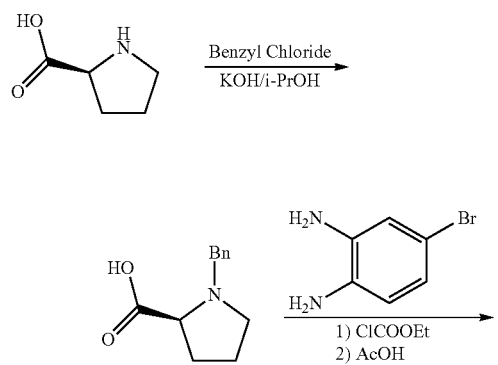

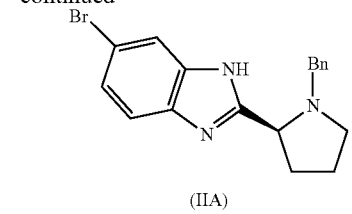

A solution of 10 g of L-proline and KOH (10 g) in 120 mL isopropanol was stirred at 40° C., then benzyl chloride (13.5 mL) was added dropwise. The reaction mixture was stirred for 6 additional hours, then neutralized with concentrated HCl to a pH of 5-6. The reaction mixture was extracted with CH$_2$Cl$_2$ (3×70 mL), the combined organic layers were washed with brine, dried over anhydrous magnesium sulfate, the solids were removed by filtration and the solvents of the filtrate were removed under reduced pressure. The residue was treated with acetone to afford N-benzyl proline (15 g).

N-Benzyl proline (10.2 g, 50 mmol) and triethylamine (50 mmol) were dissolved in THF (250 mL) and cooled to 0° C. To this solution was added ethyl chloroformate (ClCOOEt, 50 mmol) dropwise over 15 minutes and stirred for an additional 30 minutes. To this solution was added 4-bromobenzene-1,2-diamine (75 mmol) over 15 minutes. The reaction mixture was stirred at 0° C. for 1 hour, then was allowed to reach room temperature and stirred for 16 hours, then refluxed for 3 hours. After completion of this reaction, the mixture was cooled to room temperature and diluted with ethyl acetate (3×70 mL). The organic layers were combined, dried (magnesium sulfate), the solids were removed by filtration and the solvents of the filtrate were evaporated under reduced pressure. The residue was purified by column chromatography (hexanes/ethyl acetate: 7/3) to afford 11 g of intermediate.

11 g of intermediate was dissolved in acetic acid (50 mL) at 20° C. and stirred for 15 hours. The solvent was removed under reduced pressure and then NaHCO$_3$ (saturated, aqueous, 200 mL) was added. The resulting mixture was extracted with ethyl acetate (3×80 mL). The combined organic layers were concentrated and the residue was purified by column chromatography to afford 3 g of IIA.

Example 3

Synthesis of Compounds of Formula I

3.1. Preparation of Compound No. 1

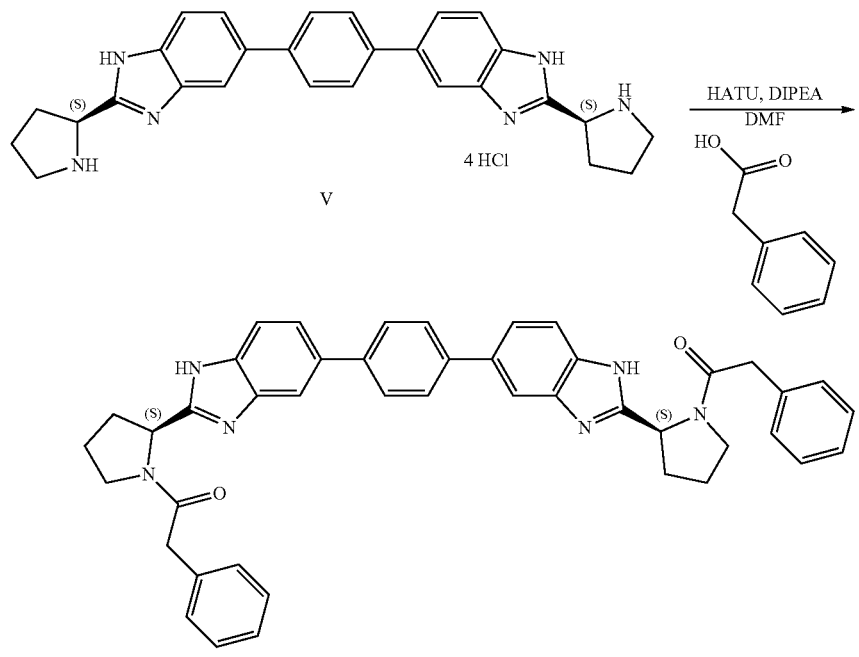

To a solution of V (400 mg, 0.77 mmol) in DMF (10 mL) was added DIPEA (0.5 mL, 3 mmol), HATU (0.73 g, 1.9 mmol) and phenylacetic acid (2.2 eq, 230 mg, 1.7 mmol). The mixture was stirred for 2 hours at room temperature and then purified via solid phase extraction (Waters PoraPak CX 60 cc, washed with 3 volumes of methanol before use). The crude reaction mixture was loaded, rinsed with methanol (4 volumes) and then eluted with 7M ammonia in methanol (solution from Aldrich, 4 volumes). The eluate was evaporated under reduced pressure to afford a tan foam. To achieve a fine solid, HCl (3 mL, 5 to 6M in isopropanol, Acros) was added and subsequently the solvents were removed azeotropically with toluene to afford a tan solid.

LCMS (M+H) m/z=685 for VI having the formula $C_{44}H_{40}N_6O_2$

Alternatively, purification and work-up of the reaction can be carried out as follows: add $CH_2Cl_2$, wash with saturated $NaHCO_3$, dry the organic phase with $Na_2SO_4$, filter and concentrate in vacuo. The residue is then purified by silicagel chromatography (0-10% MeOH in $CH_2Cl_2$) or by preparative HPLC.

3.2 Preparation of Compounds 2 to 62

Compounds 2 to 62 listed in table 1 were synthesized using the procedure for compound 1 described in example 3.1 using the appropriate carboxylic acid of formula R—C(═O)—OH.

All compounds were characterized by LC/MS. The following LC/MS methods were used:

Method A: Waters Acquity UPLC equipped with a PDA detector (range 210-400 nm) and a Waters SQD with a dual mode ion source ES+/−. The column used was a Halo C18, 2.7μ, 2.1×50 mm, and held at 50° C. A gradient of 95% aqueous formic acid (0.1%)/5% acetonitrile to 100% acetonitrile was ramped over 1.5 minutes, held for 0.6 minutes, then returns to 100% aqueous formic acid (0.1%) for 0.5 minutes. The flow rate was 0.6 mL/min.

Method B: Liquid Chromatography: Waters Alliance 2695, UV detector:Waters 996 PDA, range:210-400 nm; Mass detector: Waters ZQ, ion source: ES+, ES− Column used: SunFire C18 3.5μ 4.6×100 mm mobile phase A: 10 mM $NH_4OOCH+0.1\%$ HCOOH in $H_2O$; mobile phase B: $CH_3OH$; column temp.: 50° C.; flow: 1.5 mL/min gradient time(min) [% A/% B] 0 [65/35] to 7[5/95] to 9.6[5/95] to 9.8[65/35] to 12 [65/35]

Method C: Waters Acquity UPLC equipped with a PDA detector (range 210-400 nm) and a Waters SQD with a dual mode ion source ES+/−.: The column used was a XS Strategy 1.7μ, 2.1×20 mm, and held at 50° C. A gradient of 100% aqueous formic acid (0.1%) to 100% acetonitrile was ramped over 1.5 minutes, held for 0.6 minutes, then returns to 100% aqueous formic acid (0.1%) for 0.5 minutes. The flow rate was 0.6 mL/min.

Method D: XTerra MS $C_{18}$ 2.5μ 4.6×50 mm; mobile phase A: 10 mM $NH_4OOCH+0.1\%$ HCOOH in $H_2O$; mobile phase B: $CH_3OH$; column temp.: 50° C.; flo: 1.5 ml/min gradient time(min) [% A/% B] 0 [65/35] to 3.8 [5/95] to 5.5[5/95] to 5.6[65/35] to 7 [65/35].

Some compounds were characterized by $^1H$ NMR

Compound 2: $^1H$ NMR (400 MHz, DMSO-$d_6$, major isomer described): 12.14-12.30 (2H, m), 7.70-7.85 (6H, m), 7.44-7.62 (4H, m), 7.24 (2H, d, J=8.0 Hz), 5.15-5.28 (2H, m), 4.26-4.38 (2H, m), 3.81-3.98 (4H, m), 3.56 (6H, s), 3.47-3.54 (2H, m), 3.20 (6H, s), 2.15-2.32 (4H, m), 2.15-2.32 (4H, m), 1.09 (6H, d, J=6.0 Hz).

Compound 30: $^1$H NMR (400 MHz, DMSO-d$_6$, major isomer described): 12.13-12.77 (2H, m), 7.73-7.80 (6H, m), 7.47-7.60 (4H, m), 7.32 (2H, d, J=8.6 Hz), 5.17-5.24 (2H, m), 4.05-4.15 (2H, m), 3.80-3.91 (4H, m), 3.55 (6H, s), 2.18-2.31 (4H, m), 1.87-2.13 (6H, m), 0.80-0.92 (12H, m).

Compound 40: $^1$H NMR (400 MHz, DMSO-d$_6$, major isomer described): 12.13-12.25 (2H, m), 7.42-7.87 (12H, m), 5.12-5.26 (2H, m), 3.97-4.07 (2H, m), 3.69-3.89 (4H, m), 3.55 (6H, s), 2.15-2.31 (4H, m), 1.89-2.14 (4H, m), 1.05-1.19 (2H, m) 0.31-0.50 (8H, m).

TABLE 1 compounds of formula I

| Compound No. | Y (* denotes point of attachment) | Exact Mass | Observed Mass (M + H) | Rt (Minutes) [method] |
|---|---|---|---|---|
| 1 | | 684.32 | 685 | 0.89[A] |
| 2 | | 794.38 | 795 | 5.32[B] |
| 3 | | 644.31 | 645 | 0.69[C] |
| 4 | | 798.36 | 799 | 5.54[B] |
| 5 | | 838.33 | 839 | 0.58[C] |
| 6 | | 772.37 | 773 | 0.81[C] |
| 7 | | 716.31 | 717 | 0.83[C] |

TABLE 1-continued compounds of formula I

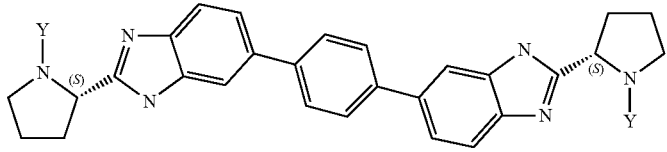

| Compound No. | Y (* denotes point of attachment) | Exact Mass | Observed Mass (M + H) | Rt (Minutes) [method] |
|---|---|---|---|---|
| 8 | 2-fluorophenylpropanoyl | 748.33 | 749 | 1.0[C] |
| 9 | 1-(methoxycarbonylamino)cyclopropanecarbonyl | 730.32 | 731 | 4.51[B] |
| 10 | (3,5-difluoro-4-methoxyphenyl)acetyl | 816.30 | 817 | 0.98[C] |
| 11 | (2-(trifluoromethoxy)phenyl)acetyl | 852.29 | 853 | 1.08[C] |
| 12 | (pyridin-3-yl)acetyl | 686.31 | 687 | 0.59[C] |
| 13 | 3-(pyridin-3-yl)propanoyl | 714.34 | 715 | 0.7[C] |
| 14 | (S)-tetrahydrofuran-2-carbonyl | 644.31 | 645 | 0.69[C] |
| 15 | phenylglyoxyloyl | 712.28 | 713 | 0.62[C] |

TABLE 1-continued compounds of formula I

| Compound No. | Y (* denotes point of attachment) | Exact Mass | Observed Mass (M + H) | Rt (Minutes) [method] |
|---|---|---|---|---|
| 16 | benzo[1,3]dioxol-5-ylacetyl group | 772.30 | 773 | 0.87[C] |
| 17 | (S)-2-(diethylamino)-2-phenylacetyl group | 826.47 | 827 | 3.42[B] |
| 18 | 3-(dimethylamino)propanoyl group | 646.37 | 647 | 0.57[C] |
| 19 | 2-(1H-imidazol-1-yl)-2-phenylacetyl group | 816.36 | 817 | 0.71[C] |
| 20 | (S)-2-phenyl-2-(piperidin-1-yl)acetyl group | 850.47 | 851 | 3.51[B] |
| 21 | furan-3-carbonyl group | 636.25 | 637 | 0.61[C] |
| 22 | (S)-2-phenyl-2-(propanoylamino)acetyl group | 826.40 | 827 | 0.91[C] |

TABLE 1-continued compounds of formula I

| Compound No. | Y (* denotes point of attachment) | Exact Mass | Observed Mass (M + H) | Rt (Minutes) [method] |
|---|---|---|---|---|
| 23 | *N-methylcarbamoyl-valine derivative* | 760.42 | 761 | 5.30[B] |
| 24 | 2,5-dimethyloxazole-4-carbonyl | 694.30 | 695 | 0.8[C] |
| 25 | pyridine-2-carbonyl | 658.28 | 659 | 0.61[C] |
| 26 | N,N-dimethyl-leucinoyl | 730.47 | 731 | 0.69[C] |
| 27 | 4-fluorobenzoyl | 692.27 | 693 | 0.74[C] |
| 28 | N,N-dimethyl-valinoyl | 702.44 | 703 | 0.63[C] |
| 29 | cyclohexylacetyl | 696.42 | 697 | 1.07[C] |
| 30 | methoxycarbonyl-valine derivative | 762.39 | 763 | 0.71[C] |
| 31 | pyridine-3-carbonyl | 658.28 | 659 | 0.56[C] |

TABLE 1-continued compounds of formula I

[Structure: a symmetric molecule with two benzimidazole groups linked via a central phenylene, each benzimidazole bearing an (S)-pyrrolidinyl group with N-Y substituent]

| Compound No. | Y (* denotes point of attachment) | Exact Mass | Observed Mass (M + H) | Rt (Minutes) [method] |
|---|---|---|---|---|
| 32 | methyl (R)-(1-oxo-3-methylbutan-2-yl)carbamate group | 762.39 | 763 | 0.80[C] |
| 33 | (S)-2-hydroxy-3-methylbutanoyl group | 648.34 | 649 | 3.01[D] |
| 34 | (R)-2-hydroxy-2-phenylacetyl group | 716.31 | 717 | 5.42[B] |
| 35 | 2-hydroxy-3-(pyridin-3-yl)propanoyl group | 746.33 | 747 | 2.32[D] |
| 36 | (R)-2-(dimethylamino)-2-phenylacetyl group | 770.41 | 771 | 3.24[B] |
| 37 | methyl (S)-(3,3-dimethyl-1-oxobutan-2-yl)carbamate group | 790.42 | 791 | 6.42[B] |
| 38 | (R)-2-((tert-butoxycarbonyl)amino)-2-phenylacetyl group | 914.45 | 915 | 7.40[B] |

TABLE 1-continued
compounds of formula I
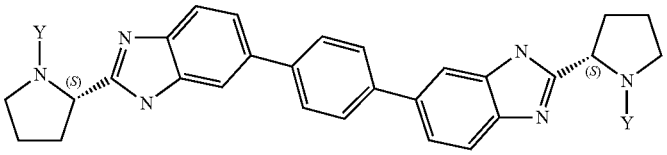
| Compound No. | Y (* denotes point of attachment) | Exact Mass | Observed Mass (M + H) | Rt (Minutes) [method] |
|---|---|---|---|---|
| 39 | 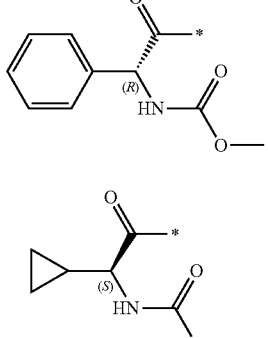 | 830.35 | 831 | 5.99[B] |
| 40 | 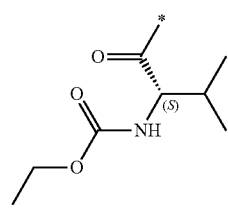 | 758.35 | 759 | 5.34[B] |
| 41 | 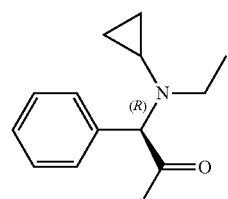 | 790.42 | 791 | 0.94[A] |
| 42 | 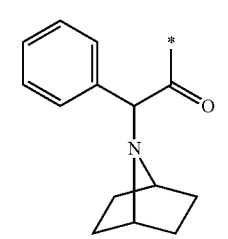 | 850.47 | 851 | 0.78[A] |
| 43 | 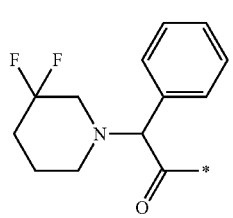 | 874.47 | 875 | 0.76[A] |
| 44 | | 922.43 | 923 | 1.13[A] |

TABLE 1-continued compounds of formula I

| Compound No. | Y (* denotes point of attachment) | Exact Mass | Observed Mass (M + H) | Rt (Minutes) [method] |
|---|---|---|---|---|
| 45 | (R)-2-phenyl-2-(pyrrolidin-1-yl)acetyl | 822.44 | 823 | 0.72[A] |
| 46 | (R)-2-morpholino-2-phenylacetyl | 854.43 | 855 | 0.71[A] |
| 47 | 2-(4-chlorophenyl)-2-(phenylamino)acetyl | 934.33 | 935 | 1.33[A] |
| 48 | (R)-2-(2-chlorophenyl)-2-hydroxyacetyl | 784.23 | 785 | 0.91[A] |
| 49 | (R)-2-(3-chlorophenyl)-2-hydroxyacetyl | 784.23 | 785 | 0.92[A] |
| 50 | (R)-2-acetamido-2-phenylpropanoyl | 826.4 | 827 | 0.91[A] |
| 51 | (S)-2-((methoxycarbonyl)amino)-4-methoxybutanoyl | 794.38 | 795 | 0.78[A] |

TABLE 1-continued compounds of formula I

| Compound No. | Y (* denotes point of attachment) | Exact Mass | Observed Mass (M + H) | Rt (Minutes) [method] |
|---|---|---|---|---|
| 52 | isopropyl carbamate-Val | 818.45 | 819 | 1.02[A] |
| 53 | propionyl-Val | 758.43 | 759 | 0.85[A] |
| 54 | (2-oxotetrahydropyrimidin-1-yl)-Val | 812.45 | 813 | 0.79[A] |
| 55 | methyl carbamate tetrahydropyran-Gly | 846.41 | 847 | 0.78[A] |
| 56 | methyl carbamate-Leu | 790.42 | 791 | 0.95[A] |
| 57 | methyl carbamate-β-hydroxy-Val | 794.38 | 795 | 0.78[A] |
| 58 | N-propyl methyl carbamate-phenylGly | 914.45 | 915 | 1.21[A] |

TABLE 1-continued compounds of formula I

| Compound No. | Y (* denotes point of attachment) | Exact Mass | Observed Mass (M + H) | Rt (Minutes) [method] |
|---|---|---|---|---|
| 59 | (valine-based acetamide group, S) | 730.4 | 731 | 0.78[A] |
| 60 | (threonine-like OH, methyl carbamate, S,R) | 766.34 | 767 | 0.71[A] |
| 61 | (threonine-like OH, methyl carbamate, S,S) | 766.34 | 767 | 0.72[A] |
| 62 | (tryptophan methyl carbamate, S) | 936.41 | 937 | 0.97[A] |

BIOLOGICAL EXAMPLES

Anti-HCV Activity of Compounds of formula I

Replicon Assay

The compounds of formula (I) were examined for inhibitory activity in the HCV replicon. This cellular assay is based on a bicistronic expression construct, as described by Lohmann et al. (1999) Science vol. 285 pp. 110-113 with modifications described by Krieger et al. (2001) Journal of Virology 75: 4614-4624, in a multi-target screening strategy.

In essence, the method was as follows:

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is flanked by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. $EC_{50}$ values were then calculated, which represent the amount of compound required to decrease the level of detected luciferase activity by 50%, or more specifically, to reduce the ability of the genetically linked HCV replicon RNA to replicate.

Results

Table 2 shows the replicon results obtained for compounds of the examples given above.

| STRUCTURE | Compound nr. | HCV-REP-HUH7LUC_EC$_{50}$ (μM) |
|---|---|---|
| 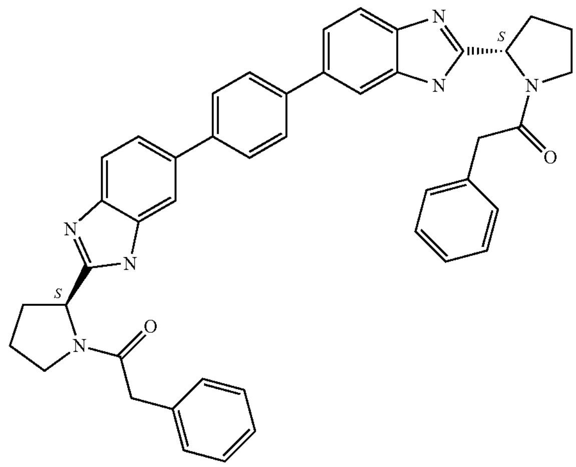 | 1 | 0.00010 |
| 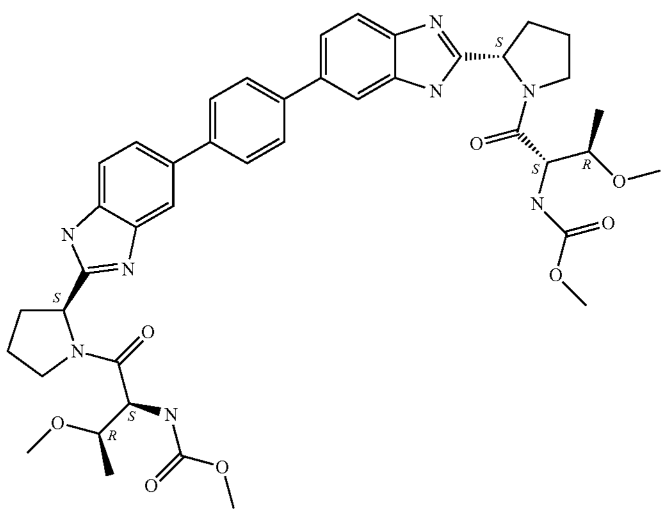 | 2 | 0.000021 |
| 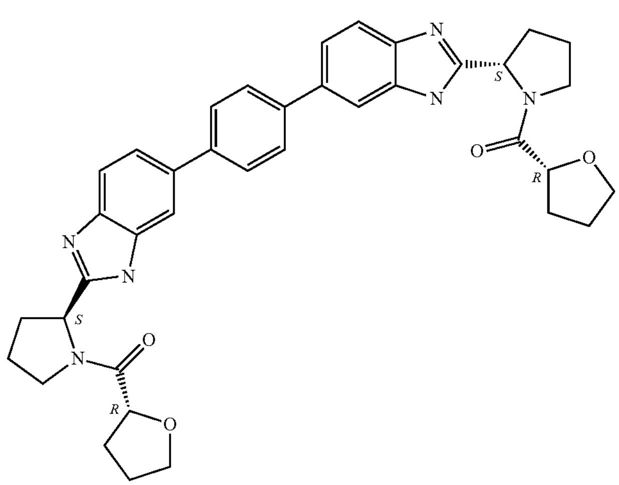 | 3 | 0.020 |

-continued

| STRUCTURE | Compound nr. | HCV-REP-HUH7LUC_EC$_{50}$ ($\mu$M) |
|---|---|---|
| 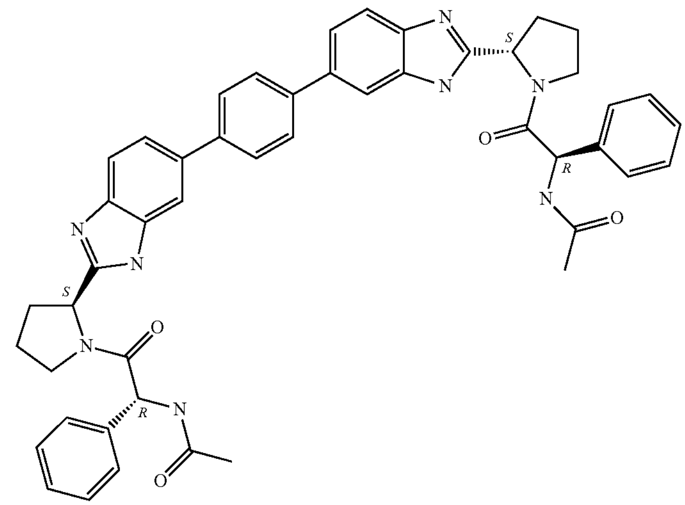 | 4 | 0.00018 |
| 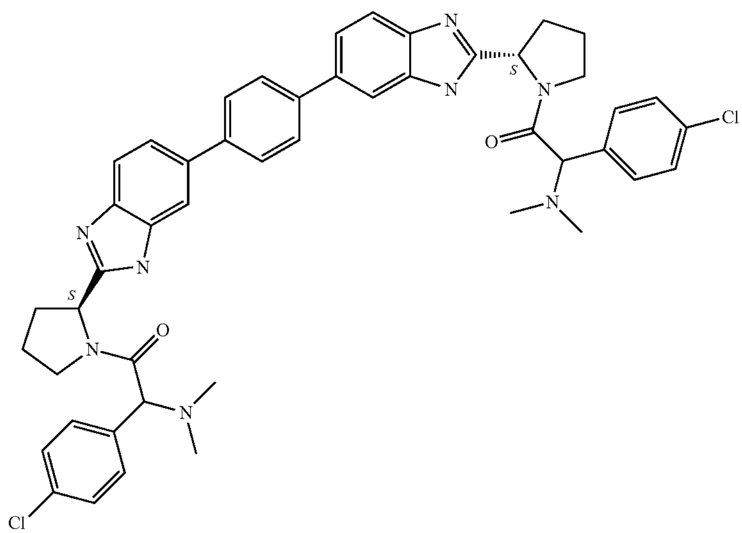 | 5 | 0.00059 |
| 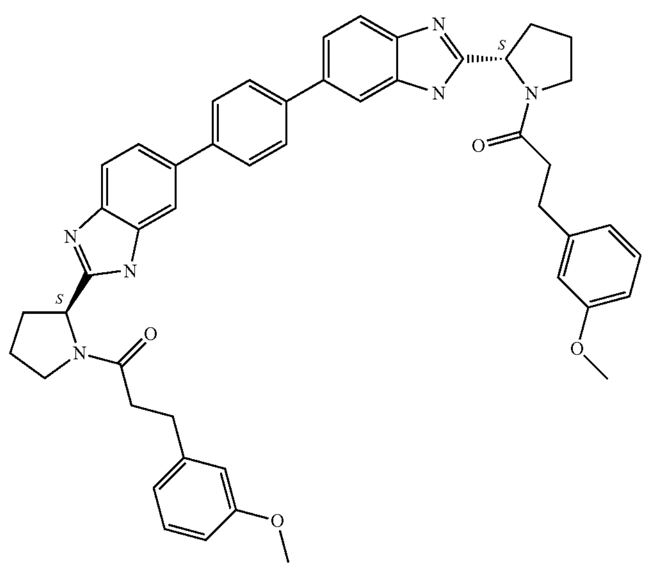 | 6 | 0.50 |

-continued

| STRUCTURE | Compound nr. | HCV-REP-HUH7LUC_EC$_{50}$ (μM) |
|---|---|---|
| 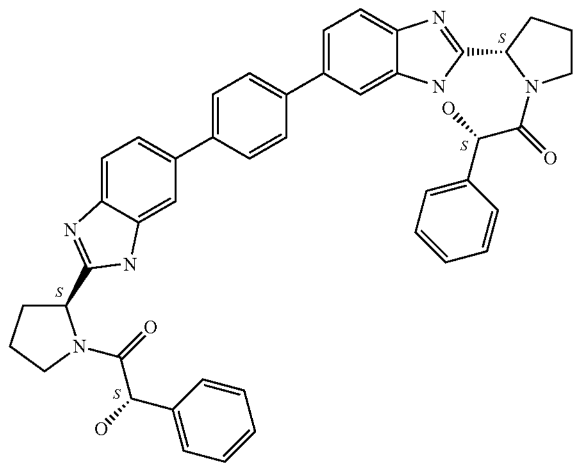 | 7 | 0.000057 |
| 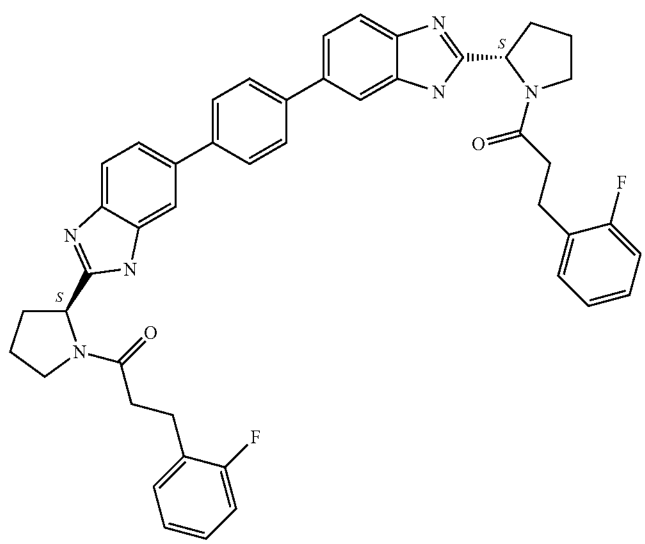 | 8 | 0.16 |
| 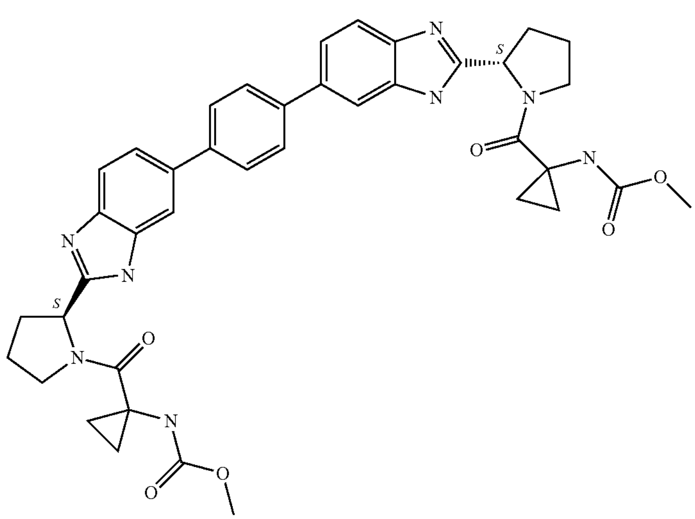 | 9 | 0.0010 |

-continued

| STRUCTURE | Compound nr. | HCV-REP-HUH7LUC_EC$_{50}$ (μM) |
|---|---|---|
| 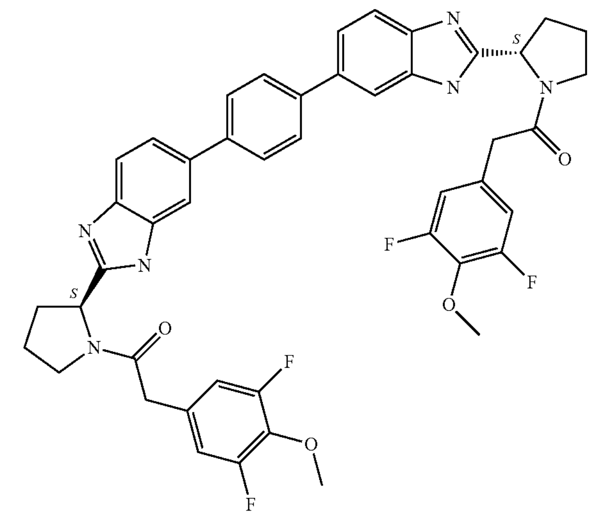 | 10 | 0.13 |
| 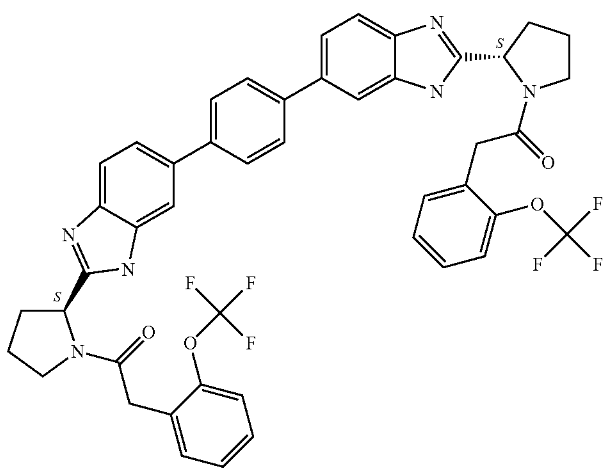 | 11 | 0.16 |
| 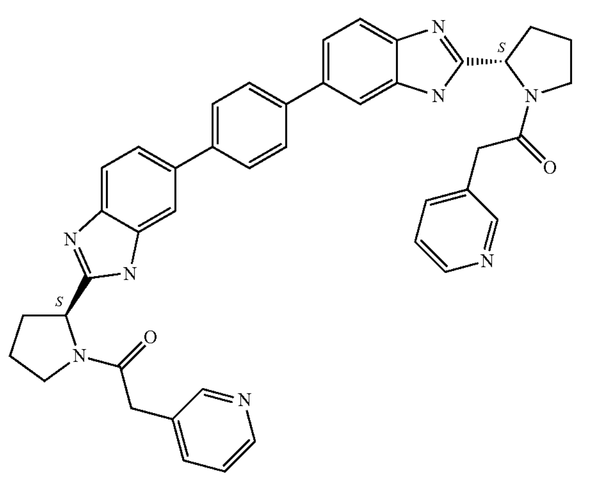 | 12 | 0.00015 |

-continued

| STRUCTURE | Compound nr. | HCV-REP-HUH7LUC_EC$_{50}$ (μM) |
|---|---|---|
| 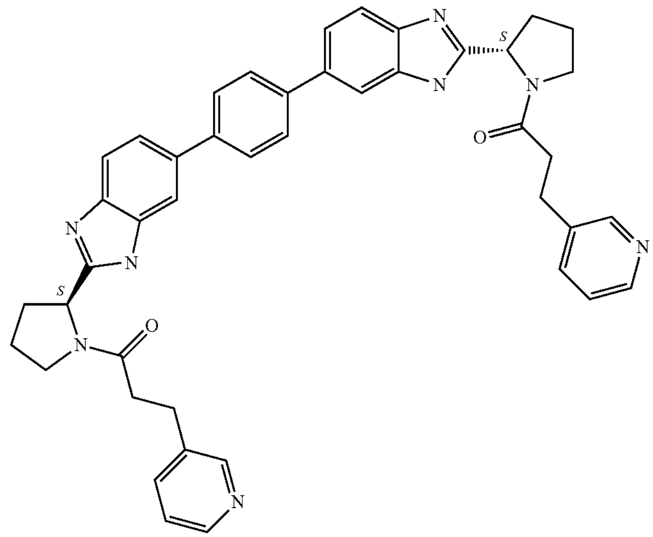 | 13 | 0.00050 |
| 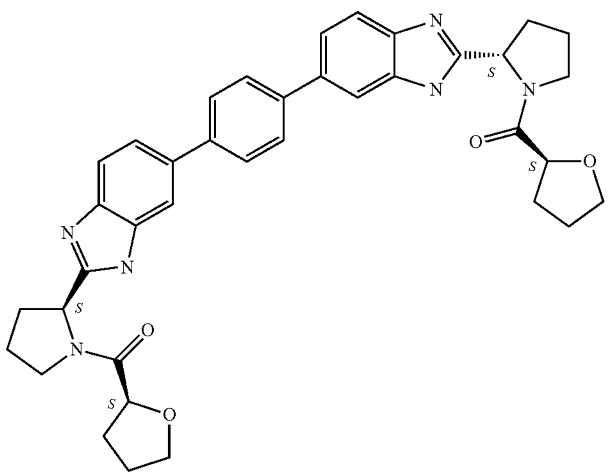 | 14 | 0.036 |
| 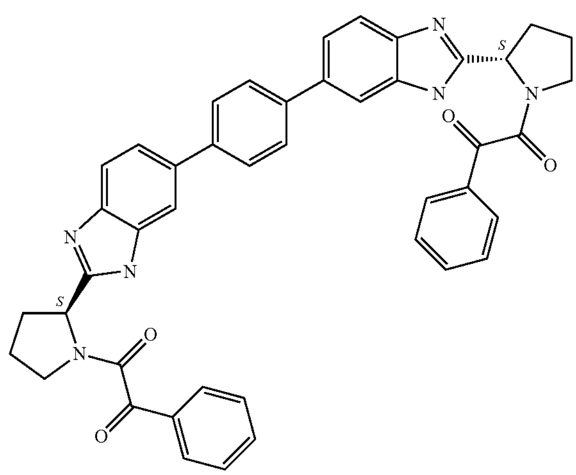 | 15 | 0.040 |

-continued

| STRUCTURE | Compound nr. | HCV-REP-HUH7LUC_EC$_{50}$ (μM) |
|---|---|---|
| 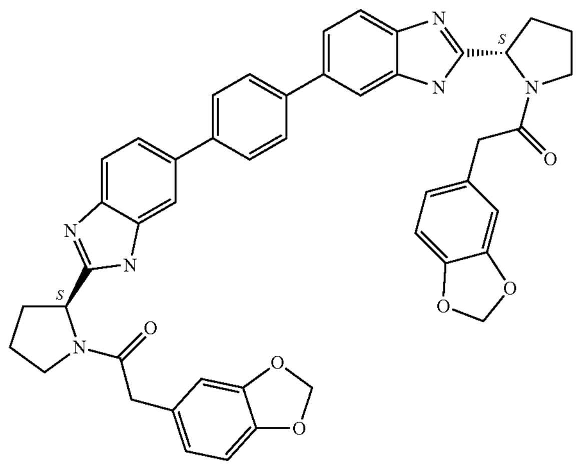 | 16 | 0.069 |
| 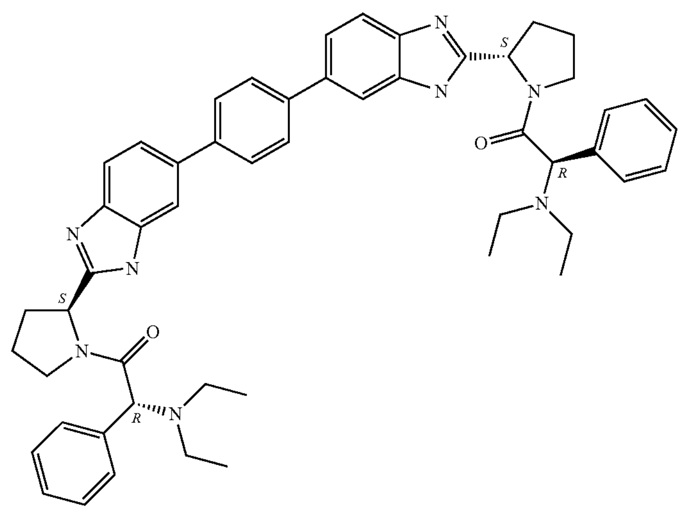 | 17 | 0.000030 |
| 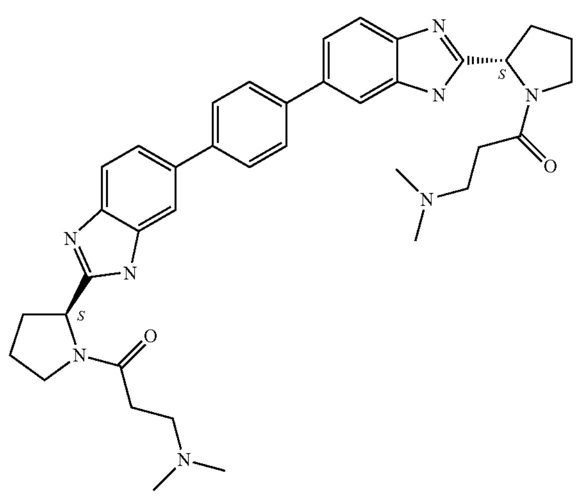 | 18 | 0.049 |

-continued

| STRUCTURE | Compound nr. | HCV-REP-HUH7LUC_EC$_{50}$ (μM) |
|---|---|---|
| 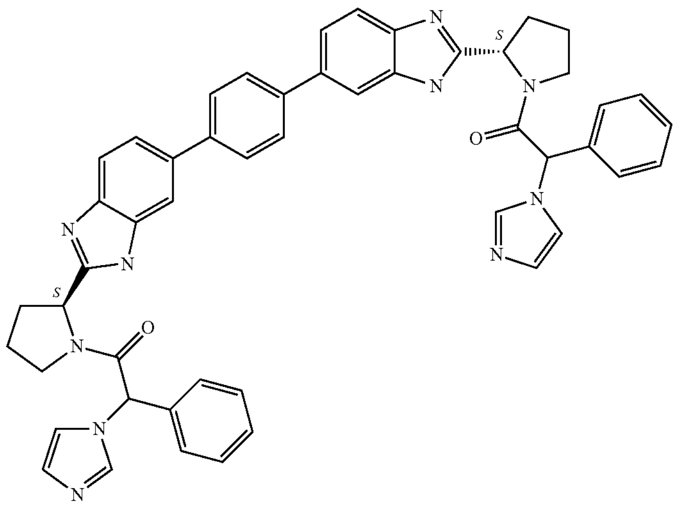 | 19 | 0.00045 |
| 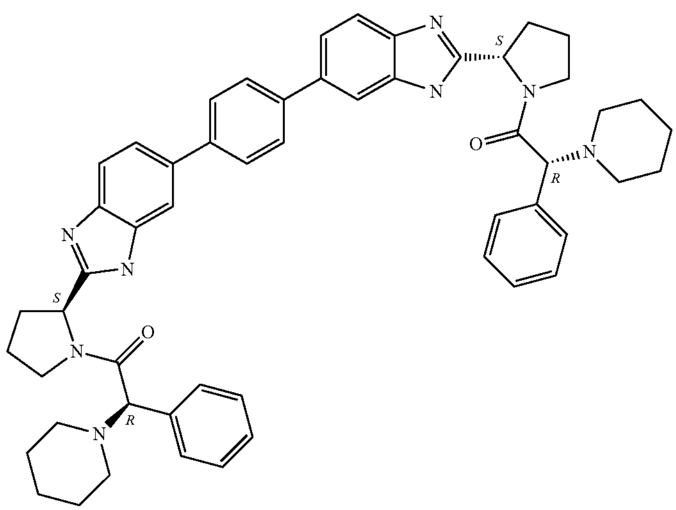 | 20 | 0.000061 |
| 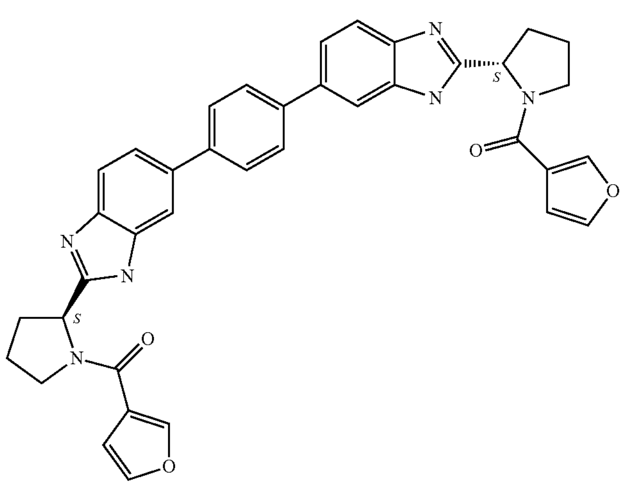 | 21 | 0.058 |

-continued

| STRUCTURE | Compound nr. | HCV-REP-HUH7LUC_EC$_{50}$ (μM) |
|---|---|---|
| 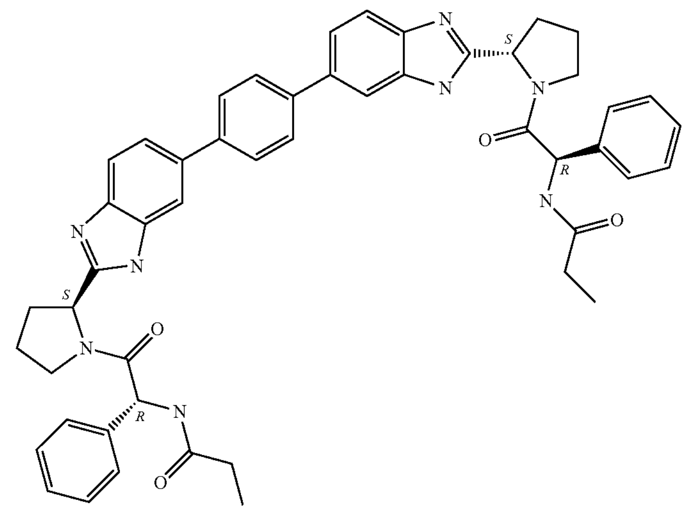 | 22 | 0.000034 |
| 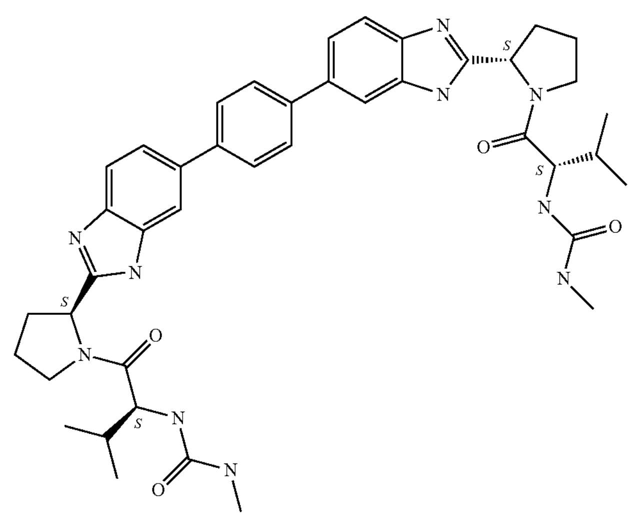 | 23 | 0.00057 |

-continued

| STRUCTURE | Compound nr. | HCV-REP-HUH7LUC_EC$_{50}$ (μM) |
|---|---|---|
| 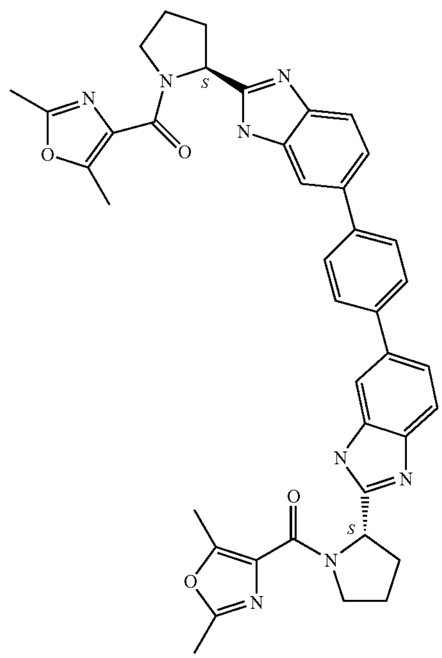 | 24 | 0.0014 |
| 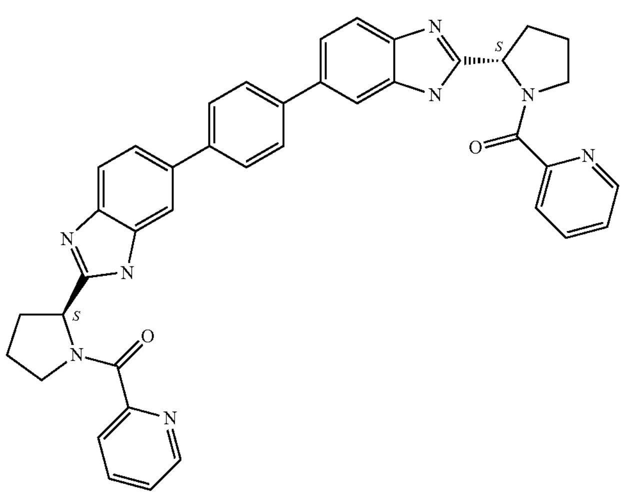 | 25 | 0.0017 |

-continued

| STRUCTURE | Compound nr. | HCV-REP-HUH7LUC_$EC_{50}$ (µM) |
|---|---|---|
| 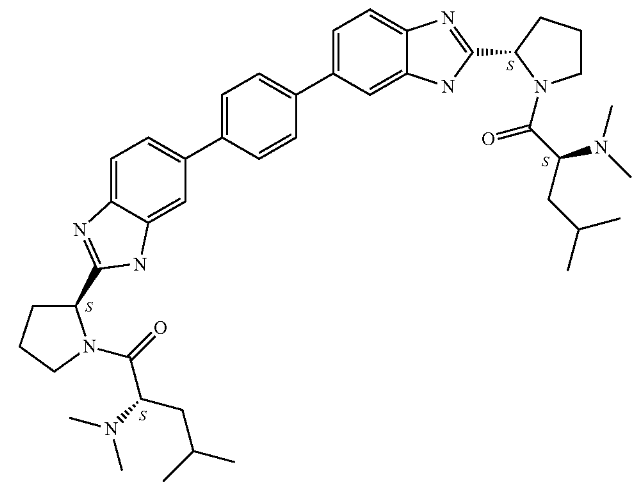 | 26 | 0.076 |
| 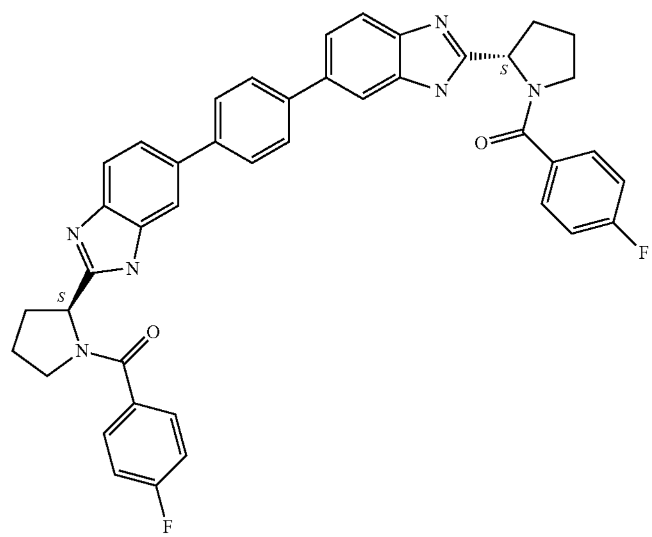 | 27 | 0.24 |
| 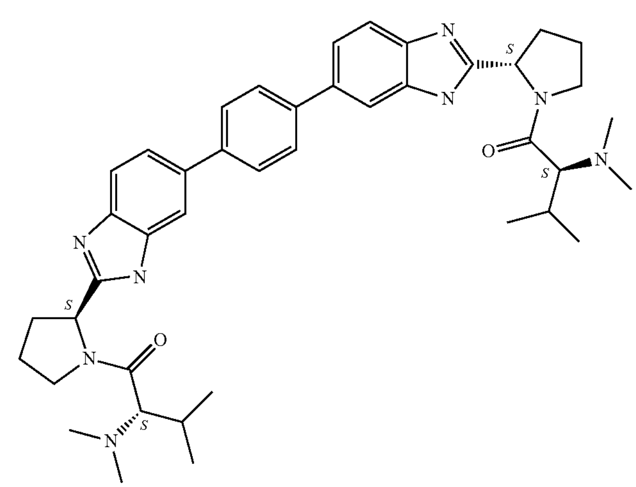 | 28 | 0.070 |

-continued

| STRUCTURE | Compound nr. | HCV-REP-HUH7LUC_EC$_{50}$ (μM) |
|---|---|---|
| 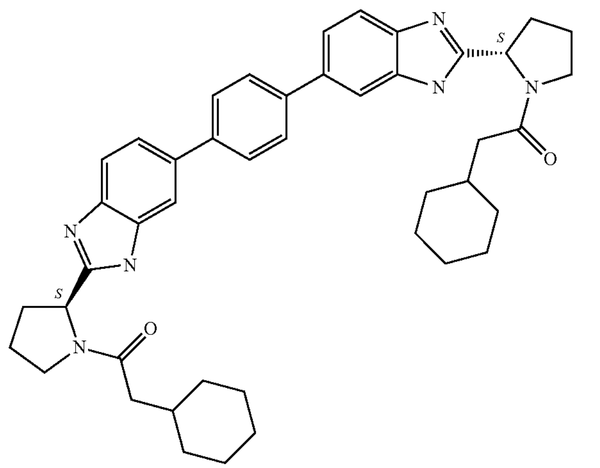 | 29 | 0.55 |
| 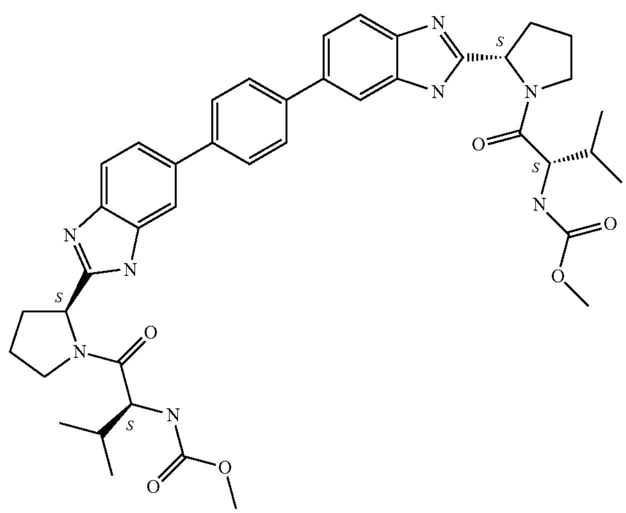 | 30 | 0.0000060 |
| 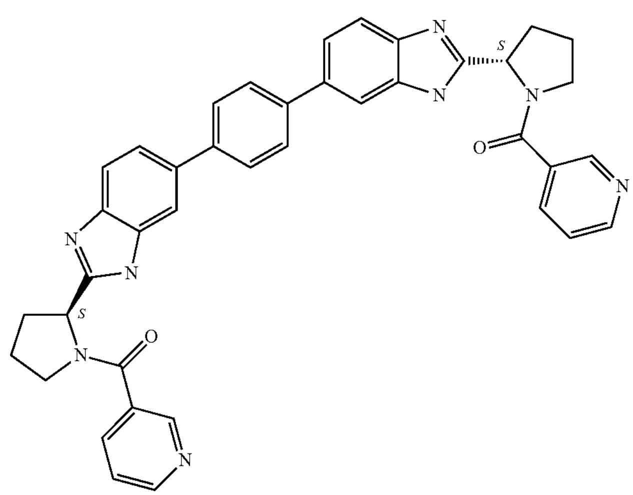 | 31 | 0.28 |

-continued

| STRUCTURE | Compound nr. | HCV-REP-HUH7LUC_EC$_{50}$ (μM) |
|---|---|---|
| 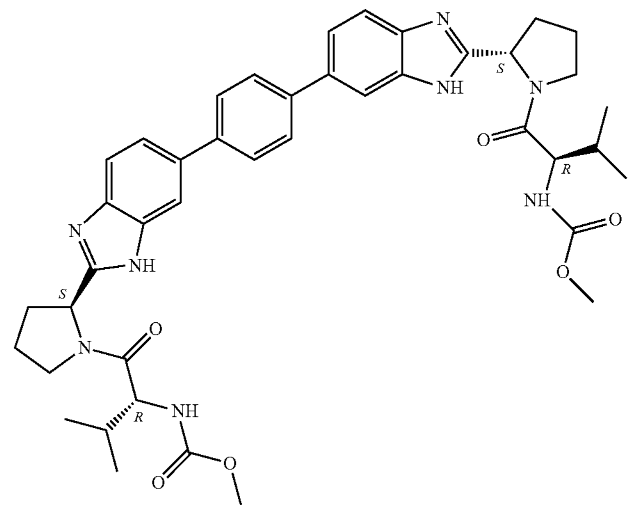 | 32 | 0.0069 |
| 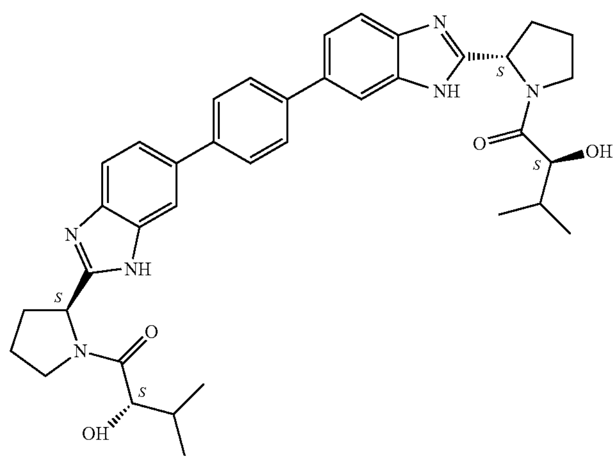 | 33 | 0.11 |
| 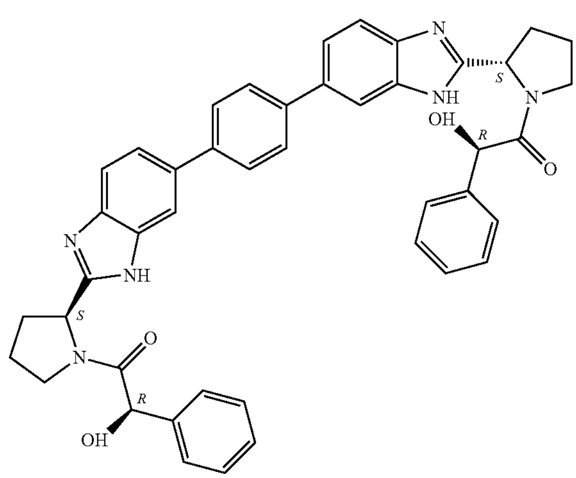 | 34 | 0.0000037 |

-continued

| STRUCTURE | Compound nr. | HCV-REP-HUH7LUC_EC$_{50}$ (μM) |
|---|---|---|
| 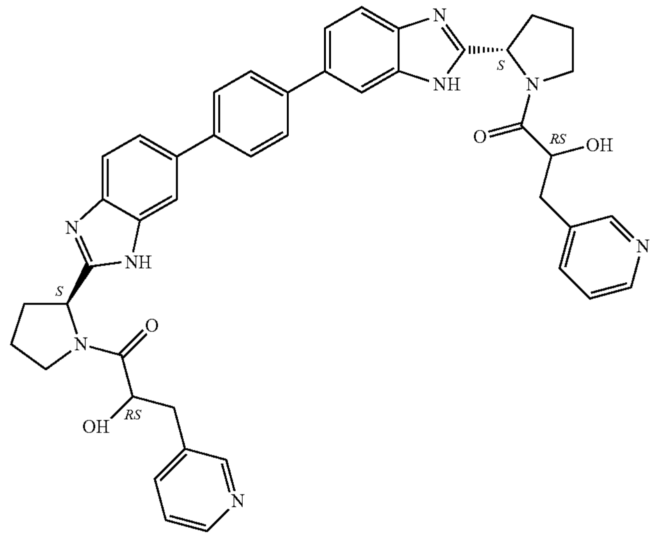 | 35 | 0.022 |
| 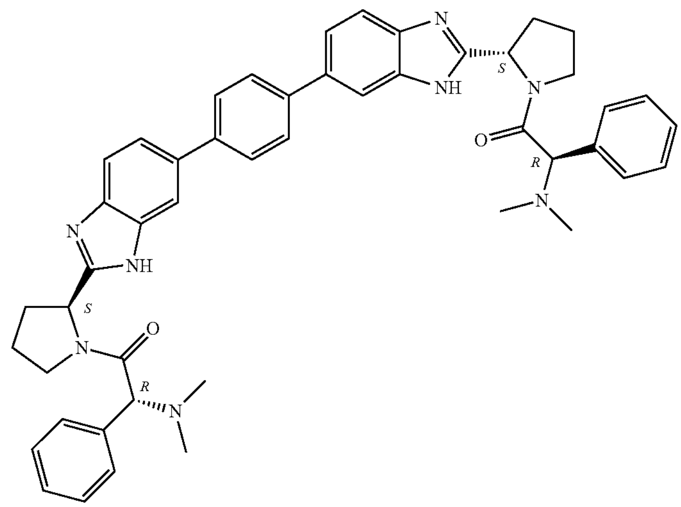 | 36 | 0.000073 |
| 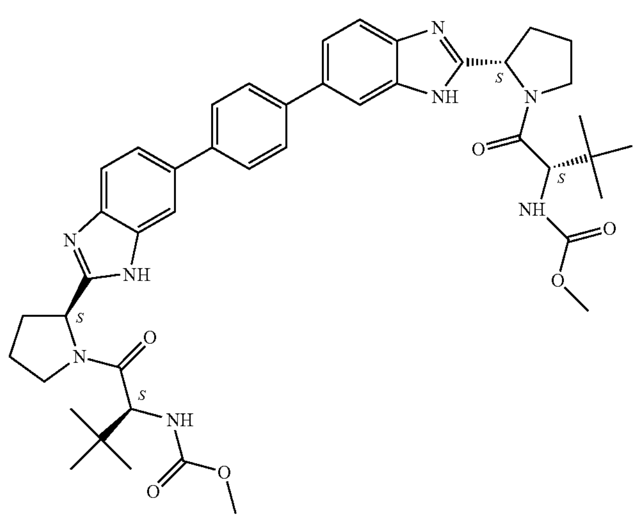 | 37 | 0.00001 |

-continued

| STRUCTURE | Compound nr. | HCV-REP-HUH7LUC_EC$_{50}$ (μM) |
|---|---|---|
| 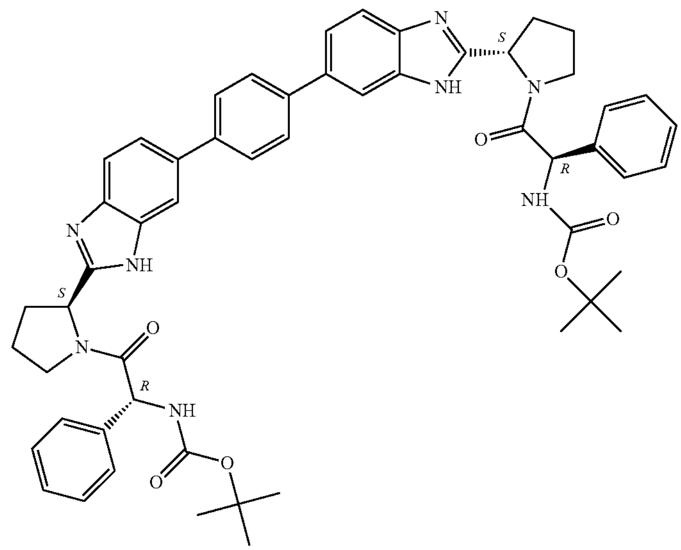 | 38 | 0.000014 |
| 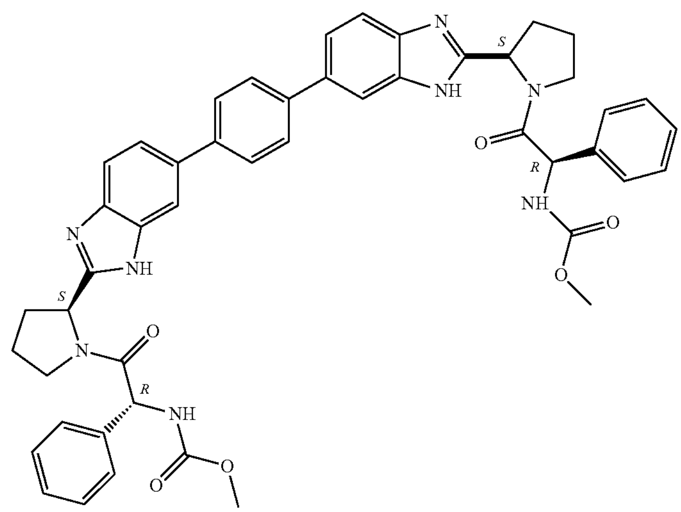 | 39 | 0.0000067 |
| 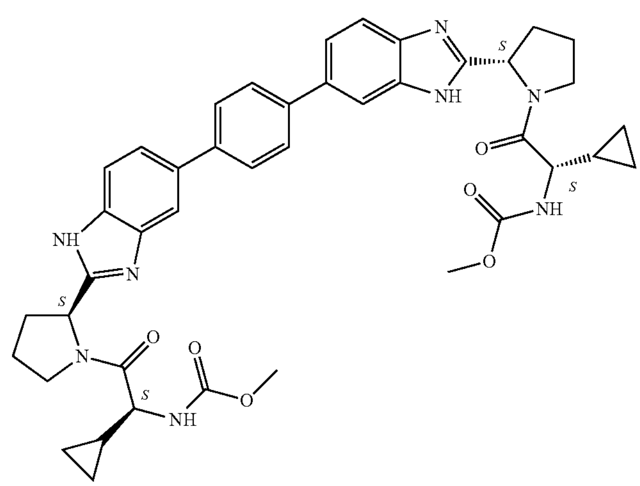 | 40 | 0.000014 |

-continued
| STRUCTURE | Compound nr. | HCV-REP-HUH7LUC_EC$_{50}$ (μM) |
|---|---|---|
| 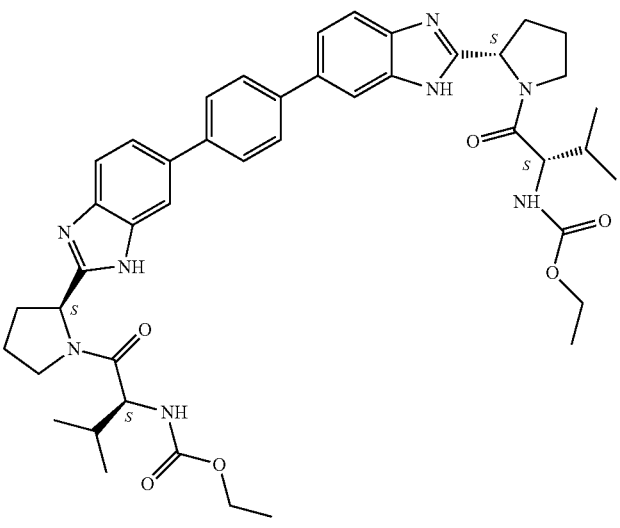 | 41 | 0.017 |
| 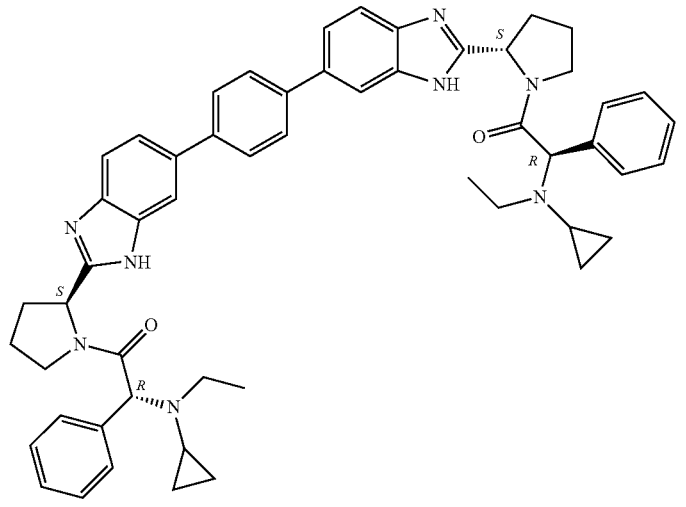 | 42 | 0.000063 |

-continued
| STRUCTURE | Compound nr. | HCV-REP-HUH7LUC_EC$_{50}$ (μM) |
|---|---|---|
| 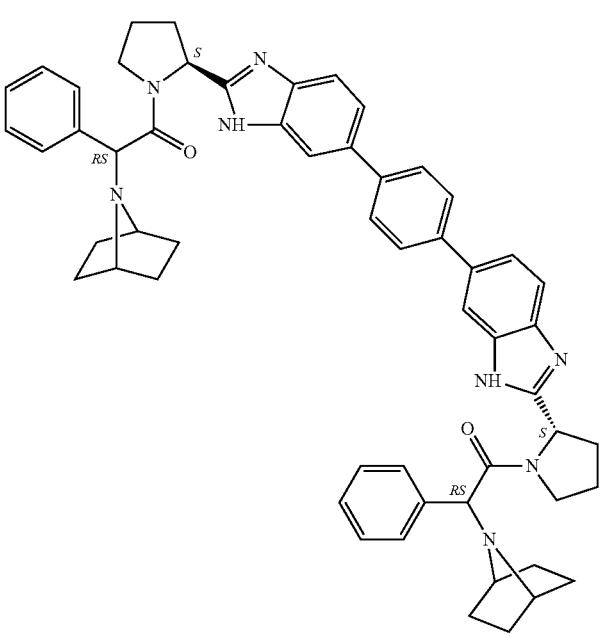 | 43 | 0.0032 |
| 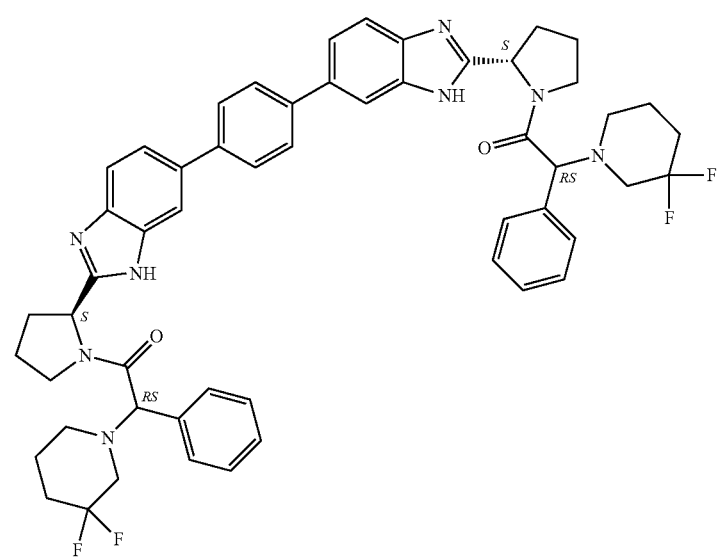 | 44 | 0.00022 |

-continued

| STRUCTURE | Compound nr. | HCV-REP-HUH7LUC_EC$_{50}$ (μM) |
|---|---|---|
| 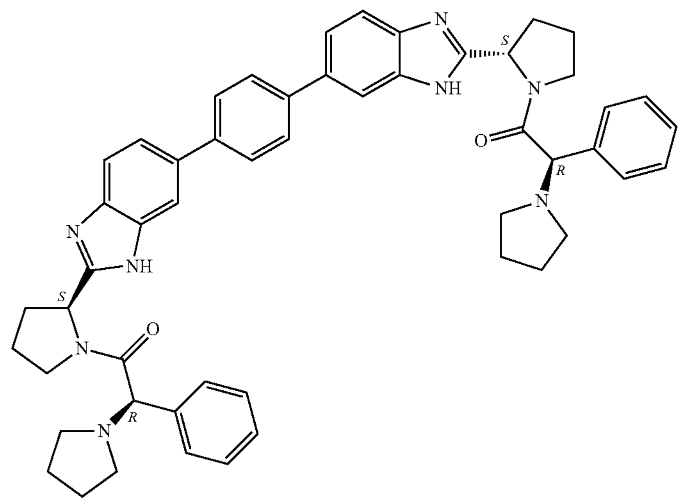 | 45 | 0.000051 |
| 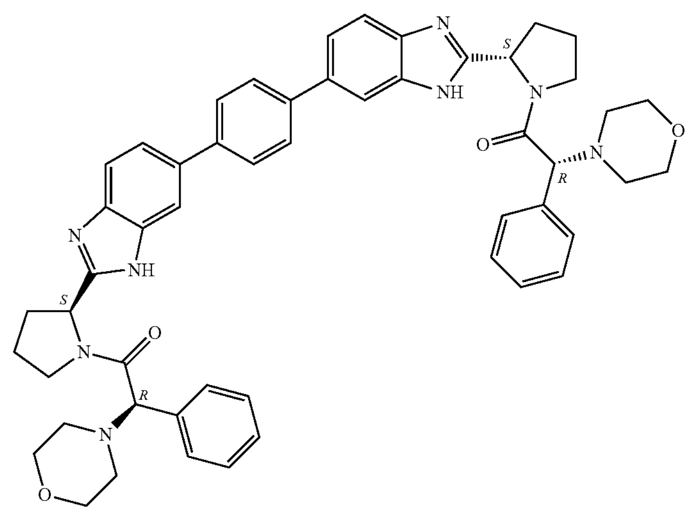 | 46 | 0.000022 |
| 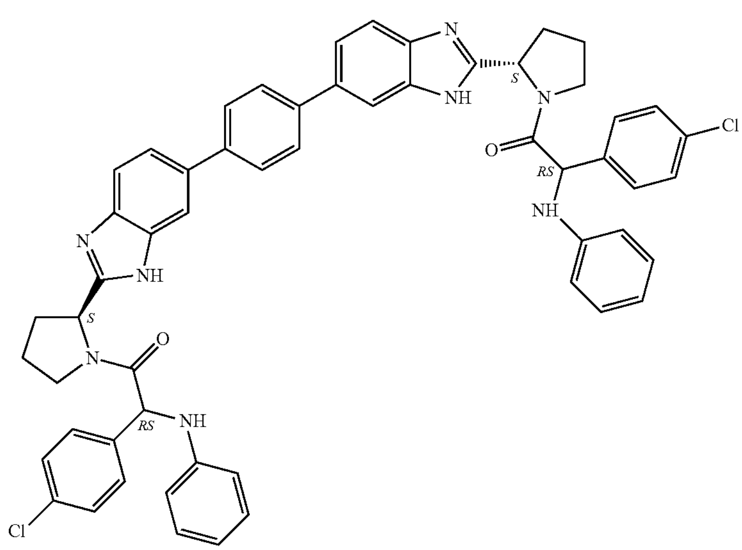 | 47 | 0.0015 |

-continued

| STRUCTURE | Compound nr. | HCV-REP-HUH7LUC_EC$_{50}$ (μM) |
|---|---|---|
| 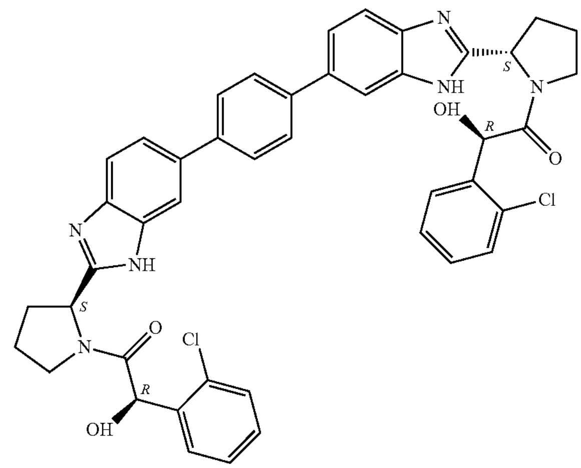 | 48 | 0.000011 |
| 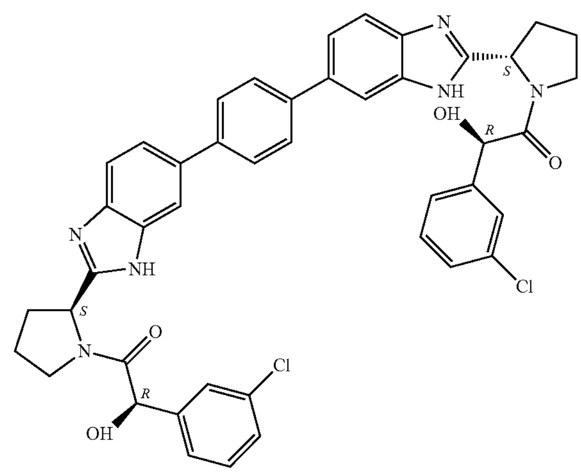 | 49 | 0.000027 |
| 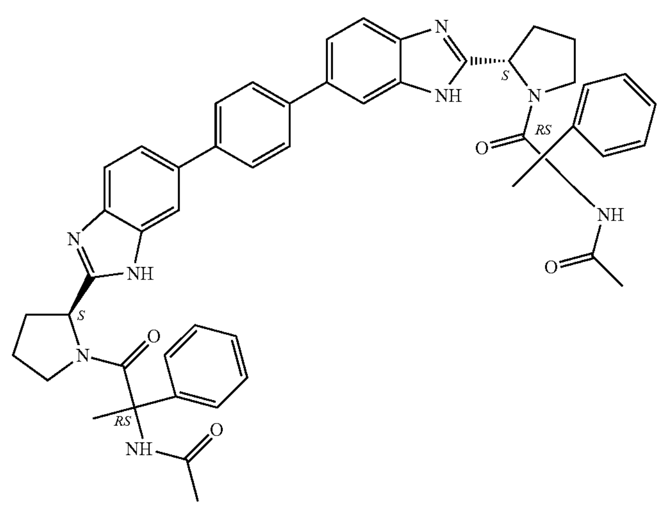 | 50 | 0.000016 |

-continued

| STRUCTURE | Compound nr. | HCV-REP-HUH7LUC_EC$_{50}$ (μM) |
|---|---|---|
| 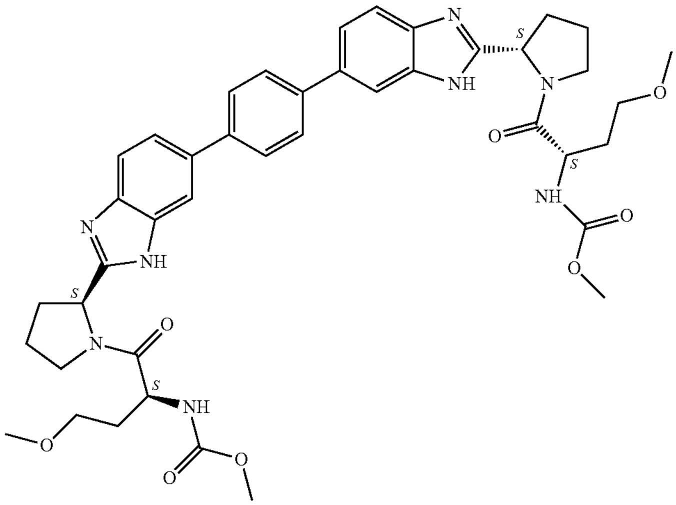 | 51 | 0.000012 |
| 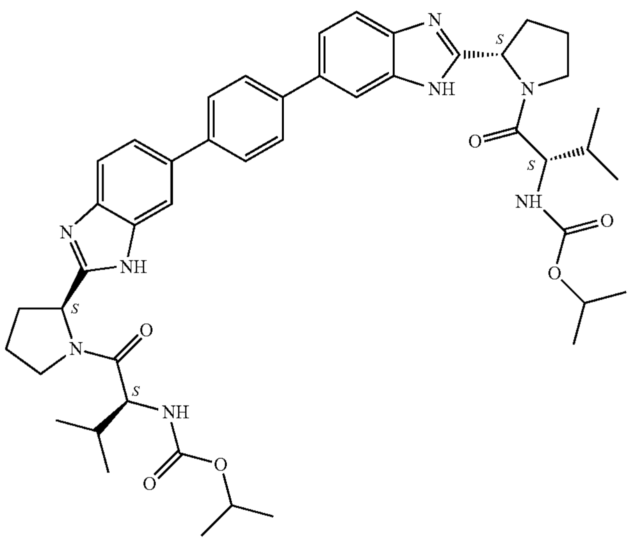 | 52 | >0.098 |
| 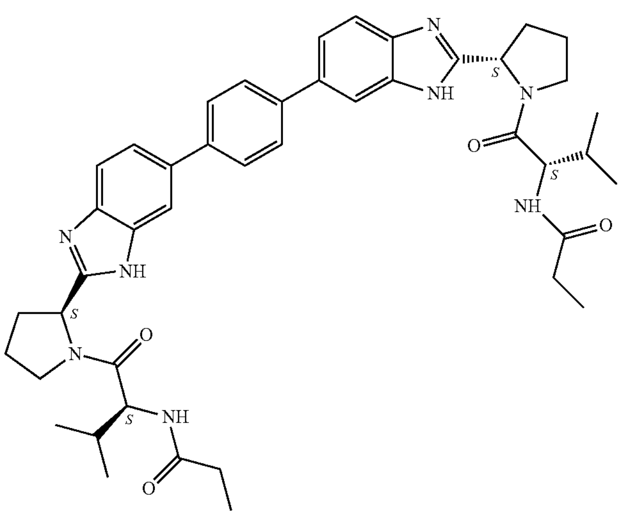 | 53 | 0.0040 |

-continued

| STRUCTURE | Compound nr. | HCV-REP-HUH7LUC_EC$_{50}$ (μM) |
|---|---|---|
| 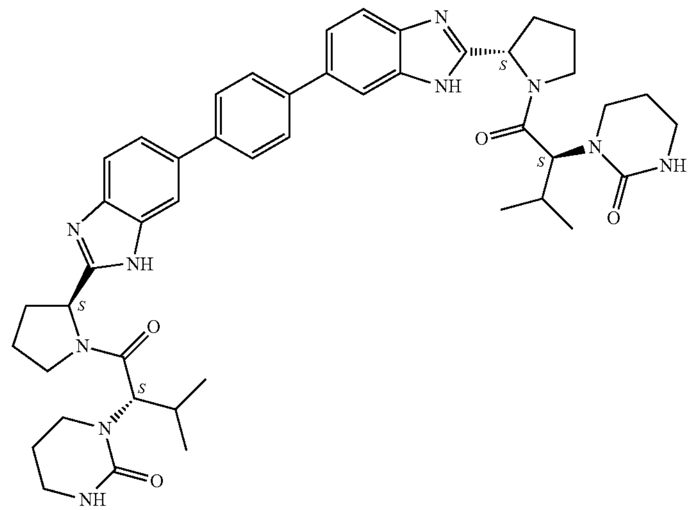 | 54 | 0.000065 |
| 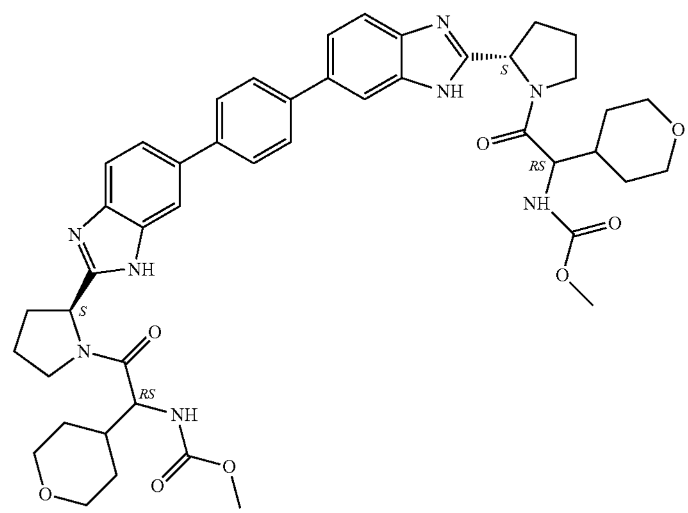 | 55 | 0.00018 |
| 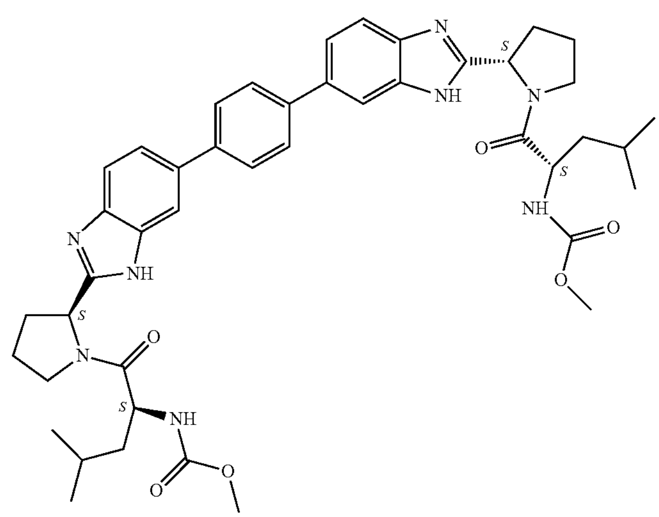 | 56 | 0.000012 |

-continued

| STRUCTURE | Compound nr. | HCV-REP-HUH7LUC_EC$_{50}$ (μM) |
|---|---|---|
| 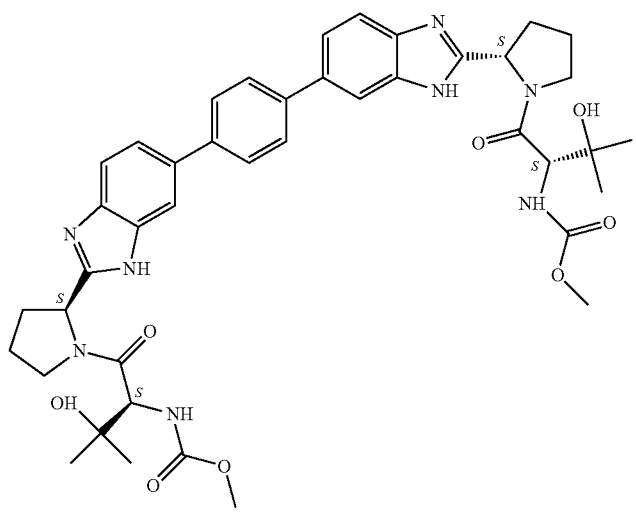 | 58 | 0.000045 |
| 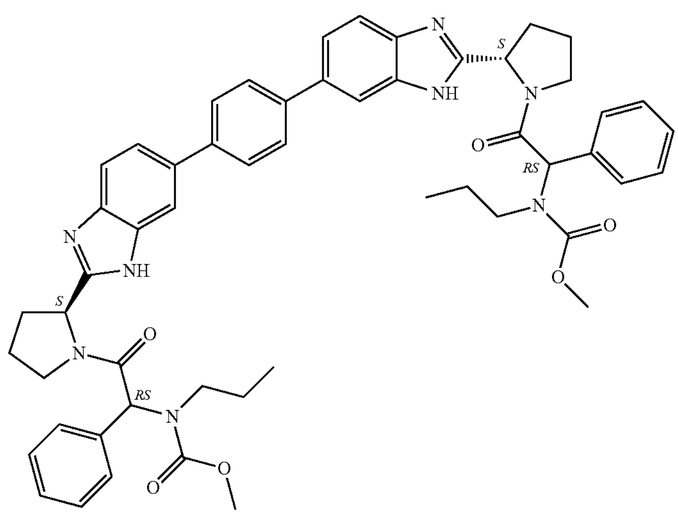 | 59 | >0.098 |
| 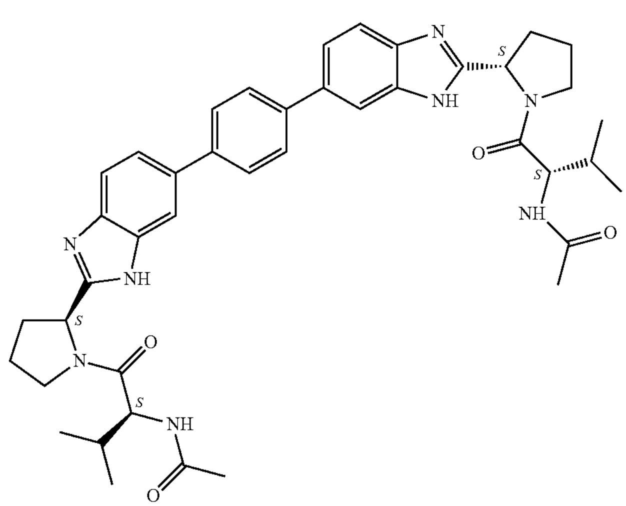 | 60 | 0.001 |

-continued

| STRUCTURE | Compound nr. | HCV-REP-HUH7LUC_EC$_{50}$ (μM) |
|---|---|---|
| 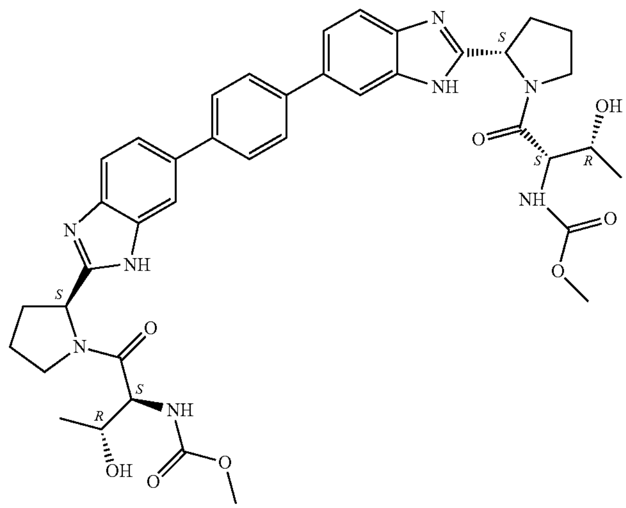 | 61 | 0.00023 |
| 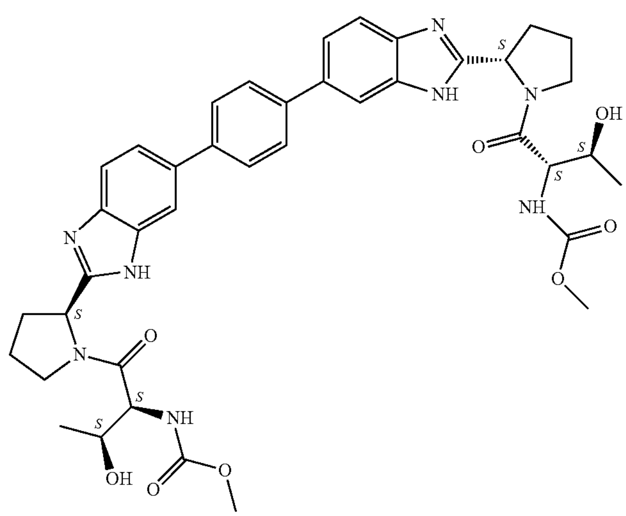 | 62 | 0.00037 |

| STRUCTURE | Compound nr. | HCV-REP-HUH7LUC_$EC_{50}$ (μM) |
|---|---|---|
| 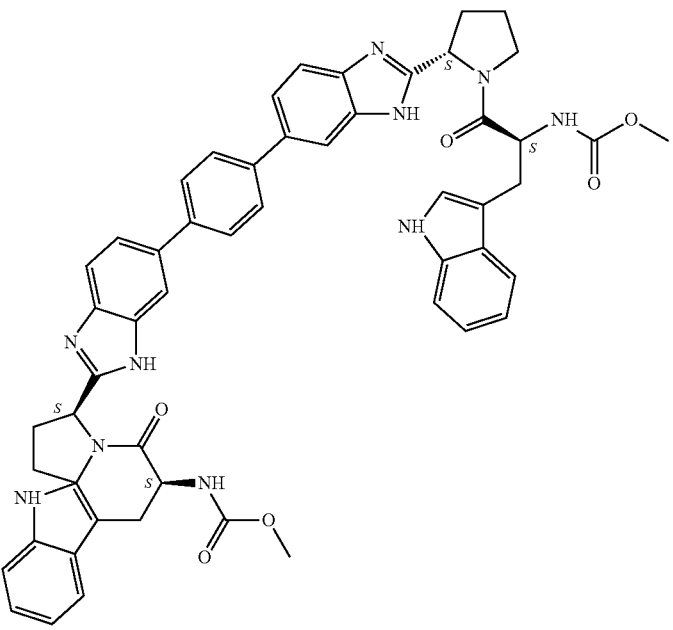 | 63 | 0.000044 |

Inhibitor Combination Studies

In a preferred embodiment, the combination of compounds described herein with another agent that alters HCV viral replication may act synergistically or antagonistically. Interactions of compounds may be analyzed by a variety of mechanistic and empirical methods.

One approach of analyzing such combinations is by three-dimensional graphs and synergistic volume calculations produced by MacSynergy™ II based on the Bliss Independency model (Dr. Mark Pritchard, University of Alabama, Tuscaloosa, Ala.). As such, compounds described herein in combination with another agent that alters HCV viral replication are said to act synergistically or have a synergistic effect when values expressed in $nM^2\%$ (volume of synergy) are between 25 and 50 $nM^2\%$ (minor but significant amount of synergy), between 50 and 100 $nM^2\%$ (moderate synergy) or over 100 $nM^2\%$ (strong synergy).

In certain embodiments, compound 2 is combined with a compound that inhibits replication of hepatitis C virus. Examples of such compounds include a protease inhibitor (TMC435350), or a polymerase inhibitor (nucleoside-based inhibitor: Ref 1; non-nucleoside-based inhibitor: Ref 3). The experiment was set-up in a "checkerboard" motif with one drug being titrated horizontally and the other one vertically on Huh-Luc cells containing the stably transfected HCV type 1b replicon. Each two-way combination was performed in quadruplicate and analyzed with the MacSynergy™ II software to obtain the percent synergy/antagonism volumes (expressed as $nM^2\%$).

In MacSynergy™ II, theoretical calculations of additive interactions are derived from dose response curves of each individual compound. The calculated additive surface is then subtracted from the experimental surface to obtain a synergy surface. Mere additive interactions would result in a horizontal plane at 0%. A peak above the 0% plane indicates synergy, a depression below the 0% plane refers to antagonism. The 95% confidence interval for the experimental dose-response surfaces was calculated to evaluate the statistical significance of the synergy or antagonism.

Combinations were tested within the concentration range mentioned in Table 3. Volumes obtained by MacSynergy™ II upon combination of compound 2 with TMC435350, Ref 1 or Ref 3 are minor, moderate or strongly synergistic, respectively. Given that synergy volumes range derived from the 95% confidence envelope for Bliss independence for combinations with TMC435350 and Ref 1 span the volume ranges determined as synergistic and Bliss independent, these tested combinations are considered to act additive to synergistic. In case of the combination with Ref 3 this synergy volumes range is synergistic (Table 4). In all instances no significant antagonism was observed.

TABLE 3

Compound range tested

| Compound | Concentration range nM |
|---|---|
| Compound 2 | 0.250-0.024 |
| TMC435350 | 75.0-7.2 |
| Ref. 1 | 36000.0-3400.0 |
| Ref. 3 | 600.0-57.0 |

TABLE 4

Synergy/antagonism volumes upon combination
as derived by MacSynergy ™ II

| Compound combination | Synergy/Antagonism volumes (95% confidence interval) nM²% | |
|---|---|---|
| Compound 2 + TMC435350 | 47.99 (87.54-8.44) | −6.05 NS* |
| Compound 2 + Ref. 1 | 79.01 (140.23-17.79) | −0.35 NS* |
| Compound 2 + Ref. 3 | 122.59 (180.43-64.15) | −0.32 (0--−1) |

*NS = 'Not Significant' as referred to by MacSynergy ™ II

The invention claimed is:

1. A compound of Formula I

I including any possible stereoisomers thereof, wherein:
R and R' are independently selected from —$CR_1R_2R_3$, aryl optionally substituted with 1 or 2 substituents selected from halo and methyl, and hetero$C_{4-7}$cycloalkyl, wherein
  $R_1$ is selected from $C_{1-4}$alkyl optionally substituted with methoxy, hydroxyl or dimethylamino; $C_{3-6}$cycloalkyl; phenyl optionally substituted with 1, 2 or 3 substituents independently selected from halo, $C_{1-4}$alkoxy, trifluoromethoxy or 2 substituents on adjacent ring atoms form a 1,3-dioxolane group; benzyl optionally substituted with halo or methoxy; heteroaryl; and heteroarylmethyl;
  $R_2$ is selected from hydrogen, hydroxyl, amino, mono- and di-$C_{1-4}$alkylamino, ($C_{3-6}$cycloalkyl)($C_{1-4}$alkyl)amino, $C_{1-4}$alkylcarbonylamino, phenylamino, $C_{1-4}$alkyloxycarbonylamino, ($C_{1-4}$alkyloxycarbonyl)($C_{1-4}$alkyl)amino, $C_{1-4}$alkylaminocarbonylamino, tetrahydro-2-oxo-1(2H)-pyrimidinyl, pyrrolidin-1-yl, piperidin-1-yl, 3,3-difluoropiperidin-1-yl, morpholin-1-yl, 7-aza-bicyclo[2.2.1]hept-7-yl, and imidazol-1-yl; and
  $R_3$ is hydrogen or $C_{1-4}$alkyl, or
  $CR_2R_3$ together forms carbonyl; or
  $CR_1R_3$ forms a cyclopropyl group;
  and the pharmaceutically acceptable salts thereof;
  provided that (a) when R and R' are identical and represent —$CR_1R_2R_3$ wherein
  (a-1) $R_2$ is $C_{1-4}$alkyloxycarbonylamino and $R_3$ is hydrogen, then $R_1$ is other than unsubstituted $C_{1-4}$alkyl, or ethyl substituted with hydroxyl or methoxy; or wherein
  (a-2) $R_2$ is methyloxycarbonylamino and $R_3$ is hydrogen, then $R_1$ is other than unsubstituted phenyl; and
  (b) when R and R' are different and each independently represent —$CR_1R_2R_3$, wherein $R_1$ is phenyl or 2-propyl, $R_2$ is dimethylamine and $R_3$ is hydrogen in one —$CR_1R_2R_3$ group, then the other —$CR_1R_2R_3$ group cannot take the meaning of $R_1$ being 2-propyl and $R_2$ being methyloxycarbonylamino and $R_3$ being hydrogen.

2. The compound of formula I according to claim 1 wherein:
  R and R' are independently selected from —$CR_1R_2R_3$, wherein
  $R_1$ is selected from phenyl optionally substituted with 1, 2 or 3 substituents independently selected from halo, $C_{1-4}$alkoxy, trifluoromethoxy or 2 substituents on adjacent ring atoms form a 1,3-dioxolane group;
  $R_2$ is selected from hydroxyl, mono- and di-$C_{2-4}$alkylamino, ($C_{3-6}$cycloalkyl)($C_{1-4}$alkyl)amino, $C_{1-4}$alkylcarbonylamino, ($C_{1-4}$alkyloxycarbonyl)($C_{1-4}$alkyl)amino, $C_{1-4}$alkylaminocarbonylamino, tetrahydro-2-oxo-1(2H)-pyrimidinyl, pyrrolidin-1-yl, piperidin-1-yl, 3,3-difluoropiperidin-1-yl, morpholin-1-yl, 7-azabicyclo[2.2.1]hept-7-yl, and imidazol-1-yl; and
  $R_3$ is hydrogen or $C_{1-4}$alkyl, or $CR_2R_3$ together forms carbonyl; or $CR_1R_3$ forms a cyclopropyl group; and the pharmaceutically acceptable salts thereof.

3. The compound of formula I according to claim 1 wherein:
  $R_1$ is selected from heteroaryl; and heteroarylmethyl;
  $R_2$ is selected from hydrogen, mono- and di-$C_{1-4}$alkylamino, ($C_{3-6}$cycloalkyl)($C_{1-4}$alkyl)amino, $C_{1-4}$alkylcarbonylamino, $C_{1-4}$alkyloxycarbonylamino, ($C_{1-4}$alkyl-oxycarbonyl)($C_{1-4}$alkyl)amino, $C_{1-4}$alkylaminocarbonylamino, tetrahydro-2-oxo-1(2H)-pyrimidinyl, pyrrolidin-1-yl, piperidin-1-yl, 3,3-difluoropiperidin-1-yl, morpholin-1-yl, 7-azabicyclo[2.2.1]hept-7-yl, and imidazol-1-yl; and
  $R_3$ is hydrogen;
  and the pharmaceutically acceptable salts thereof.

4. The compound of formula I according to claim 1 wherein:
  $R_1$ is $C_{1-4}$alkyl;
  $R_2$ is selected from $C_{1-4}$alkylaminocarbonylamino, and tetrahydro-2-oxo-1(2H)-pyrimidinyl; and
  $R_3$ is hydrogen or $C_{1-4}$alkyl;
  and the pharmaceutically acceptable salts thereof.

5. The compound of formula I according to claim 1 wherein:
  $R_1$ is $C_{3-6}$cycloalkyl;
  $R_2$ is hydrogen
  and $R_3$ is hydrogen;
  and the pharmaceutically acceptable salts.

6. The compound according to claim 1 wherein R and R' are the same.

7. The compound according to claim 1 wherein the compound is of formula Ia

Ia

8. A pharmaceutical composition comprising a compound according to claim 1, and a pharmaceutically acceptable carrier.

* * * * *